(12) United States Patent
Howard et al.

(10) Patent No.: US 7,682,745 B2
(45) Date of Patent: *Mar. 23, 2010

(54) MEDICAL DEVICE HAVING LITHIUM-ION BATTERY

(75) Inventors: William G. Howard, Roseville, MN (US); Craig L. Schmidt, Eagan, MN (US); Erik R. Scott, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 996 days.

This patent is subject to a terminal disclaimer.

(21) Appl. No.: 10/978,712

(22) Filed: Oct. 29, 2004

(65) Prior Publication Data

US 2006/0093913 A1    May 4, 2006

(51) Int. Cl.
  *H01M 4/58* (2006.01)
(52) U.S. Cl. ............ 429/231.1; 429/231.3; 429/231.95; 429/231.5; 429/233; 429/245; 429/218.1; 429/223; 429/224; 607/4; 607/5; 607/7; 607/8; 607/9; 607/10; 607/11; 607/14; 607/33; 607/42; 607/43; 607/116; 607/118
(58) Field of Classification Search ............... 429/231.1, 429/231.3, 231.95, 231.5, 233, 245, 218.1, 429/223, 224; 607/4–5, 7–11, 14, 33, 42–43, 607/116, 118
See application file for complete search history.

(56) References Cited

U.S. PATENT DOCUMENTS

| | | | |
|---|---|---|---|
| 3,791,867 A | 2/1974 | Broadhead et al. | |
| 3,864,167 A | 2/1975 | Broadhead et al. | |
| 3,898,096 A | 8/1975 | Herbdy et al. | |
| 4,009,052 A | 2/1977 | Whittingham | |
| 4,048,397 A | 9/1977 | Rothbauer | |
| 4,049,887 A | 9/1977 | Whittingham | |
| 4,113,921 A | 9/1978 | Goldstein et al. | |

(Continued)

FOREIGN PATENT DOCUMENTS

EP    0 567 149 B1    10/1993

(Continued)

OTHER PUBLICATIONS

Prosini et al. "Li4Ti5O12 as anode in all-solid-state, plastic, lithium-ion batteries for low-power applications". Solid state Ionics, Diffusion and Reactions (Sep. 2001), vol. 144, No. 1-2, p. 185-92.*

(Continued)

*Primary Examiner*—Laura S Weiner
(74) *Attorney, Agent, or Firm*—Scott A. Marks; Stephen W. Bauer; Foley & Lardner LLP

(57) ABSTRACT

A medical device includes a rechargeable lithium-ion battery for providing power to the medical device. The lithium-ion battery includes a positive electrode comprising a current collector and an active material comprising a material selected from the group consisting of $LiCoO_2$, $LiMn_2O_4$, $LiNi_xCo_yNi_{(1-x-y)}O_2$, $LiAl_xCo_yNi_{(1-x-y)}O_2$, $LiTi_xCo_yNi_{(1-x-y)}O_2$, and combinations thereof. The lithium-ion battery also includes a negative electrode having a current collector and an active material including a lithium titanate material. The current collector of the negative electrode includes a material selected from the group consisting of aluminum, titanium, and silver. The battery is configured for cycling to near-zero-voltage conditions without a substantial loss of battery capacity.

46 Claims, 8 Drawing Sheets

U.S. PATENT DOCUMENTS

| | | |
|---|---|---|
| 4,194,062 A | 3/1980 | Carides et al. |
| 4,202,702 A | 5/1980 | Nuss |
| 4,340,652 A | 7/1982 | Raistrick et al. |
| 4,446,212 A | 5/1984 | Kaun |
| 4,464,447 A | 8/1984 | Lazzari et al. |
| 4,507,371 A | 3/1985 | Thackeray et al. |
| 4,547,442 A | 10/1985 | Besenhard et al. |
| 4,555,456 A | 11/1985 | Kanehori et al. |
| 4,668,595 A | 5/1987 | Yoshino et al. |
| 4,764,437 A | 8/1988 | Kaun |
| 4,830,939 A | 5/1989 | Lee et al. |
| H723 H | 1/1990 | Plichta et al. |
| 5,053,297 A | 10/1991 | Yamahira et al. |
| 5,077,151 A | 12/1991 | Yasuda et al. |
| 5,147,737 A | 9/1992 | Post et al. |
| 5,147,739 A | 9/1992 | Beard |
| 5,160,712 A | 11/1992 | Thackeray et al. |
| 5,169,736 A | 12/1992 | Bittihn et al. |
| 5,176,969 A | 1/1993 | Miyabayashi et al. |
| 5,187,033 A | 2/1993 | Koshiba |
| 5,187,035 A | 2/1993 | Miyabayashi et al. |
| 5,196,279 A | 3/1993 | Tarascon |
| 5,264,201 A | 11/1993 | Dahn et al. |
| 5,284,721 A | 2/1994 | Beard |
| 5,296,318 A | 3/1994 | Gozdz et al. |
| 5,300,373 A | 4/1994 | Shackle |
| 5,322,746 A | 6/1994 | Wainwright |
| 5,340,666 A | 8/1994 | Tomantschger et al. |
| 5,401,598 A | 3/1995 | Miyabayashi et al. |
| 5,411,537 A * | 5/1995 | Munshi et al. ............... 607/33 |
| 5,418,090 A | 5/1995 | Koksbang et al. |
| 5,498,489 A | 3/1996 | Dasgupta et al. |
| 5,510,212 A | 4/1996 | Delnick et al. |
| 5,525,441 A | 6/1996 | Reddy et al. |
| 5,545,468 A | 8/1996 | Koshiba et al. |
| 5,547,785 A | 8/1996 | Yumiba et al. |
| 5,569,553 A | 10/1996 | Smesko et al. |
| 5,576,608 A | 11/1996 | Nagai et al. |
| 5,652,072 A | 7/1997 | Lamanna et al. |
| 5,670,862 A | 9/1997 | Lewyn |
| 5,691,081 A | 11/1997 | Krause et al. |
| 5,744,258 A | 4/1998 | Bai et al. |
| 5,744,264 A | 4/1998 | Barker |
| 5,776,628 A | 7/1998 | Kraft et al. |
| 5,882,218 A | 3/1999 | Reimers |
| 5,888,665 A | 3/1999 | Bugga et al. |
| 5,891,592 A | 4/1999 | Mao et al. |
| 5,911,947 A | 6/1999 | Mitchell |
| 5,935,724 A | 8/1999 | Spillman et al. |
| 5,935,728 A | 8/1999 | Spillman et al. |
| 5,968,681 A | 10/1999 | Miura et al. |
| 6,001,139 A | 12/1999 | Asanuma et al. |
| 6,001,507 A | 12/1999 | Ono et al. |
| 6,007,947 A | 12/1999 | Mayer |
| 6,022,643 A | 2/2000 | Lee et al. |
| 6,025,093 A | 2/2000 | Herr |
| 6,060,186 A | 5/2000 | Broussely et al. |
| 6,120,938 A | 9/2000 | Atsumi et al. |
| 6,139,815 A | 10/2000 | Atsumi et al. |
| 6,165,638 A | 12/2000 | Spillman et al. |
| 6,171,729 B1 | 1/2001 | Gan et al. |
| 6,203,947 B1 | 3/2001 | Peled et al. |
| 6,203,994 B1 | 3/2001 | Epps et al. |
| 6,207,327 B1 | 3/2001 | Takada et al. |
| 6,221,531 B1 | 4/2001 | Vaughey et al. |
| 6,228,536 B1 | 5/2001 | Wasynczuk |
| 6,258,473 B1 | 7/2001 | Spillman et al. |
| 6,265,100 B1 | 7/2001 | Saaski et al. |
| 6,274,271 B1 | 8/2001 | Koshiba et al. |
| 6,287,721 B1 | 9/2001 | Xie et al. |
| 6,316,145 B1 | 11/2001 | Kida et al. |
| 6,335,115 B1 | 1/2002 | Meissner |
| 6,352,798 B1 | 3/2002 | Lee et al. |
| 6,372,384 B1 | 4/2002 | Fujimoto et al. |
| 6,379,842 B1 | 4/2002 | Mayer |
| 6,451,480 B1 | 9/2002 | Gustafson et al. |
| 6,453,198 B1 * | 9/2002 | Torgerson et al. ............. 607/29 |
| 6,461,751 B1 | 10/2002 | Boehm et al. |
| 6,461,757 B1 | 10/2002 | Sasayama et al. |
| 6,475,673 B1 | 11/2002 | Yamawaki et al. |
| 6,489,062 B1 | 12/2002 | Watanabe |
| 6,528,208 B1 | 3/2003 | Thackeray et al. |
| 6,553,263 B1 | 4/2003 | Meadows et al. |
| 6,596,439 B1 | 7/2003 | Tsukamoto et al. |
| 6,645,670 B2 | 11/2003 | Gan |
| 6,645,675 B1 | 11/2003 | Munshi |
| 6,677,083 B2 | 1/2004 | Suzuki et al. |
| 6,706,445 B2 | 3/2004 | Barker et al. |
| 6,720,112 B2 | 4/2004 | Barker et al. |
| 6,730,437 B2 | 5/2004 | Leising et al. |
| 6,737,191 B2 | 5/2004 | Gan et al. |
| 6,759,168 B2 | 7/2004 | Yamasaki et al. |
| 6,761,744 B1 | 7/2004 | Tsukamoto et al. |
| 6,777,132 B2 | 8/2004 | Barker et al. |
| 6,824,920 B1 * | 11/2004 | Iwamoto et al. ........ 429/231.95 |
| 6,849,360 B2 | 2/2005 | Marple |
| 6,942,949 B2 | 9/2005 | Besenhard et al. |
| 7,029,793 B2 | 4/2006 | Nakagawa et al. |
| 7,101,642 B2 | 9/2006 | Tsukamoto et al. |
| 7,157,185 B2 | 1/2007 | Marple |
| 7,191,008 B2 | 3/2007 | Schmidt et al. |
| 7,211,350 B2 | 5/2007 | Amatucci |
| 7,337,010 B2 * | 2/2008 | Howard et al. ............. 607/116 |
| 7,459,235 B2 | 12/2008 | Choi et al. |
| 7,524,580 B1 | 4/2009 | Birke et al. |
| 2001/0008725 A1 | 7/2001 | Howard |
| 2001/0012590 A1 | 8/2001 | Ehrlich |
| 2001/0021472 A1 | 9/2001 | Barker et al. |
| 2001/0031401 A1 | 10/2001 | Yamawaki et al. |
| 2003/0025482 A1 | 2/2003 | Tsukamoto et al. |
| 2003/0104282 A1 | 6/2003 | Xing et al. |
| 2003/0124423 A1 | 7/2003 | Sasaki et al. |
| 2003/0157410 A1 | 8/2003 | Jarvis et al. |
| 2003/0215716 A1 | 11/2003 | Suzuki et al. |
| 2004/0023117 A1 | 2/2004 | Imachi et al. |
| 2004/0062989 A1 | 4/2004 | Ueno et al. |
| 2004/0072072 A1 | 4/2004 | Suzuki et al. |
| 2004/0096745 A1 | 5/2004 | Shibano et al. |
| 2004/0147971 A1 | 7/2004 | Greatbatch et al. |
| 2004/0147972 A1 | 7/2004 | Greatbatch et al. |
| 2004/0158296 A1 | 8/2004 | Greatbatch et al. |
| 2004/0168307 A1 | 9/2004 | Hong |
| 2004/0176818 A1 | 9/2004 | Wahlstrand et al. |
| 2004/0197657 A1 | 10/2004 | Spitler et al. |
| 2004/0209156 A1 | 10/2004 | Ren et al. |
| 2005/0031919 A1 | 2/2005 | Ovshinsky et al. |
| 2005/0069777 A1 * | 3/2005 | Takami et al. ............... 429/245 |
| 2005/0130043 A1 | 6/2005 | Gao et al. |
| 2005/0147889 A1 | 7/2005 | Ohzuku et al. |
| 2005/0164082 A1 | 7/2005 | Kishi et al. |
| 2005/0244716 A1 | 11/2005 | Ogawa et al. |
| 2006/0024582 A1 | 2/2006 | Li et al. |
| 2006/0046149 A1 | 3/2006 | Yong et al. |
| 2006/0068282 A1 | 3/2006 | Kishi et al. |
| 2006/0093871 A1 | 5/2006 | Howard et al. |
| 2006/0093872 A1 | 5/2006 | Howard et al. |
| 2006/0093873 A1 | 5/2006 | Howard et al. |
| 2006/0093894 A1 | 5/2006 | Scott et al. |
| 2006/0093913 A1 | 5/2006 | Howard et al. |
| 2006/0093916 A1 | 5/2006 | Howard et al. |
| 2006/0093917 A1 | 5/2006 | Howard et al. |
| 2006/0093918 A1 | 5/2006 | Howard et al. |
| 2006/0093921 A1 | 5/2006 | Scott et al. |
| 2006/0093923 A1 | 5/2006 | Howard et al. |

| | | |
|---|---|---|
| 2006/0095094 A1 | 5/2006 | Howard et al. |
| 2006/0216612 A1 | 9/2006 | Jambunathan et al. |
| 2006/0234125 A1 | 10/2006 | Valle |
| 2006/0251968 A1 | 11/2006 | Tsukamoto et al. |
| 2007/0009801 A1 | 1/2007 | Inagaki et al. |
| 2007/0059587 A1 | 3/2007 | Kishi et al. |
| 2007/0072085 A1 | 3/2007 | Chen et al. |
| 2007/0077496 A1 | 4/2007 | Scott et al. |
| 2007/0111099 A1 | 5/2007 | Nanjundaswamy et al. |
| 2007/0134556 A1 | 6/2007 | Sano et al. |
| 2007/0162083 A1 | 7/2007 | Schmidt et al. |
| 2007/0233195 A1 | 10/2007 | Wahlstrand et al. |
| 2007/0239221 A1 | 10/2007 | Kast et al. |
| 2007/0248881 A1 | 10/2007 | Scott et al. |
| 2007/0284159 A1 | 12/2007 | Takami et al. |
| 2008/0020278 A1 | 1/2008 | Schmidt et al. |
| 2008/0020279 A1 | 1/2008 | Schmidt et al. |
| 2008/0026297 A1 | 1/2008 | Chen et al. |
| 2008/0044728 A1 | 2/2008 | Schmidt et al. |
| 2009/0035662 A1 | 2/2009 | Scott et al. |

FOREIGN PATENT DOCUMENTS

| | | |
|---|---|---|
| EP | 0 732 761 A2 | 9/1996 |
| EP | 0 982 790 A1 | 3/2000 |
| EP | 1 014 465 A1 | 6/2000 |
| EP | 1 018 773 A1 | 7/2000 |
| EP | 1 068 635 A1 | 1/2001 |
| EP | 1 282 180 A1 | 2/2003 |
| EP | 1 487 039 A1 | 12/2004 |
| EP | 1 722 439 A1 | 11/2006 |
| JP | 56-136462 | 10/1981 |
| JP | 57-11476 | 1/1982 |
| JP | 63-1708 | 1/1982 |
| JP | 57-152669 | 9/1982 |
| JP | 02-309568 | 12/1990 |
| JP | 6-275263 | 9/1994 |
| JP | 10-027626 A | 1/1998 |
| JP | 2000156229 A | 6/2000 |
| JP | 2000-195499 | 7/2000 |
| JP | 2001-126756 | 5/2001 |
| JP | 2001-185141 A | 7/2001 |
| WO | WO 97/06569 A1 | 2/1997 |
| WO | WO 97/48141 | 12/1997 |
| WO | WO 00/017950 | 3/2000 |
| WO | WO 01/33656 A1 | 5/2001 |
| WO | WO 02/09215 A2 | 1/2002 |
| WO | WO 02/21628 A1 | 3/2002 |
| WO | WO 02/39524 A1 | 5/2002 |
| WO | WO 02/069414 A2 | 9/2002 |
| WO | WO 02/095845 A1 | 11/2002 |
| WO | WO 03/044880 A1 | 5/2003 |
| WO | WO 03/075371 A2 | 9/2003 |
| WO | WO 03/090293 A2 | 10/2003 |
| WO | WO 2006/050022 A2 | 5/2006 |
| WO | WO 2006/050023 A2 | 5/2006 |
| WO | WO 2006/050098 A1 | 5/2006 |
| WO | WO 2006/050099 A1 | 5/2006 |
| WO | WO 2006/050100 A2 | 5/2006 |
| WO | WO 2006/050117 A1 | 5/2006 |
| WO | WO 2006/050117 A2 | 5/2006 |
| WO | WO 2006/064344 A2 | 6/2006 |

OTHER PUBLICATIONS

Peramunage et al., Preparation of Micro-Sized $Li_4Ti_5O_{12}$ and Its Electrochemistry in Polyacrylonitrile Electrolye-Based Lithium Cells, Technical Papers, Electrochemical Science and Technology, J. Electrochem Soc., vol. 145, No. 8, Aug. 1998 © The Electrochemical Society, Inc., 7 pages.
Ohzuku et al., Zero-Strain Insertion Material of $Li[Li_{1/frax;1;3}Ti_{frax;5;3}]O_4$ for Rechargeable Lithium Cells, Electrochemical Science and Technology, J. Electrochem Soc., vol. 142, No. 5, May 1995 © The Electrochemical Society, Inc., 5 pages.
International Search Report for PCT/US2005/038970, date of mailing Oct. 25, 2006, 3 pages.
International Search Report for PCT/US2005/038761, date of mailing Oct. 4, 2006, 2 pages.
International Search Report for PCT/US2005/038762, date of mailing Oct. 2, 2006, 2 pages.
International Search Report for PCT/US2005/038942, date of mailing, Mar. 2, 2006, 3 pages.
International Search Report for PCT/US2005/038943, date of mailing, Mar. 16, 2006, 3 pages.
International Search Report for PCT/US2005/038944, date of mailing, Mar. 31, 2006, 3 pages.
Cava et al., The Crystal Structures of the Lithium-Inserted Metal Oxides $Li_{0.5}TiO_2$ Anatase, $LiTi_2O_4$ Spinel, and $Li_2Ti_2O_4$, Journal of Solid State Chemistry, vol. 53, Jan. 1984 © Academic Press, Inc., pp. 64-75.
Murphy et al., Lithium Insertion in Anatase: A New Route to the Spinel $LiTi_2O_4$, Revue De Chimie Minerale, vol. 19, 1982, 9 pgs.
Mikula et al., Photoelectrochemical Properties of Anodic $TiO_2$ Layers Prepared by Various Current Densities, J. Electrochemical Society, vol. 139, No. 12, Dec. 1992 © The Electrochemical Society, Inc., pp. 3470-3474.
Murphy et al., Ternary $Li_xTiO_2$ Phases from Insertion Reactions, Solid State Ionics, vols. 9 & 10, 1983 © North-Holland Publishing Company, pp. 413-418.
Sasaki et al., Layered Hydrous Titanium Dioxide: Potassium Ion Exchange and Structural Characterization, Inorganic Chemistry, vol. 24, No. 14, © 1982 American Chemical Society, pp. 2265-2271.
Colbow et al., Structure and Electrochemistry of the Spinel Oxides $LiTi_2O_4$ and $Li_{4/3}T_{5/3}O_4$, Journal of Power Sources, vol. 26, 1989, © Elsevier Sequoia, pp. 397-402.
Brohan et al., Properties Physiques Des Bronzes $M_xTiO_2(B)$, Solid State Ionics, vols. 9 and 10, 1983, © North Holland Publishing Company, pp. 419-424.
Murphy et al., "Topochemical Reactions of Rutile Related Structures with Lithium", Mat. Res. Bull, vol. 13, No. 12, 1978, © Pergamon Press, Inc., pp. 1395-1402.
Wang et al., Li Insertion and Ion Exchange Reactions in the Ionic Conducting Tl2(M,Ti)8O16 Phases with Hollandite-Type Structure, Technical Papers, Solid-State Science and Technology, J. Electrochem Soc., vol. 138, No. 1, Jan. 1991, © The Electrochemical Society, Inc.
Sawai, et al., Factors Affecting Rate Capability of a Lithium-ion Battery with $Li[Li_{1/3}Ti_{5/3}]O_4$ and $LiCo_{1/2}Ni_{1/2}O_2$, Abs. 75, 205th Meeting, 1 page.
Kavan, et al., Proof of Concept—$Li_4Ti_5O_{12}$, Electrochemical and Solid State Letters, 2002, vol. 5, A39-A42, p. 13.
Wang et al., Novel Eletrolytes for Nanocrystalline $Li_4Ti_5O_{12}$ Based High Power Lithium Ion Batteries.
Ohzuku, Extended Abstracts from the Seventh Int'l Meeting on Li Batteries, Boson, MA, May 15-20, 1994, pp. 111-112.
Ohzuku, et al, "Zero-Strain Insertion Material of $Li[Li_{1/3}Ti_{5/3}]O_4$ for Rechargeable Lithium Cells", J. Electrochem. Soc. vol. 142 #5, 1995, pp. 1431-1435.
Ferg et al, "Spinel Anodes for Lithium-Ion Batteries", J. Electrochem. Soc. vol. 141 #11, 1994, pp. L147-L150.
Zaghib, et al, "Electrochemical Study of $Li_4Ti_5O_{12}$ As Negative Electrode for Li-Ion Polymer Rechargeable Batteries", Journal of Power Sources, 81-82, 1999, pp. 300-305.
Jansen, et. al., "Development of A High-Power Lithium-Ion Battery", Journal of Power Sources, 81-82, 1999, pp. 902-905.
Ariyoshi, et al., "Three-Volt Lithium-Ion Battery with $Li[Ni_{1/2}Mn_{3/2}]O_4$ and the Zero-Strain Insertion Material of $Li[Li_{1/3}Ti_{5/3}]O_4$", Journal of Power Sources, 119-121, 2003, pp. 959-963.
Singhal, et al. "Nanostructured Electrodes for Next Generation Rechargeable Electrochemical Devices", Journal of Power Sources, 129, 2004, pp. 38-44.
FMC Lithium, CAS No. 74389-93-2, "Stabilized Lithium Metal Powder" Product Specification, Copyright 2001 FMC Corporation (2 pages).
Jarvis et al., "A Li-Ion Cell Containing A Non-Lithiated Cathode", Abs. 182, IMLB 12 Meeting (1 page).

Ohzuku et al., "Lithium-Ion Batteries of Li[Li$_{1/3}$Ti$_{5/3}$]O$_4$ With Selected Positive-Electrode Materials for Long-Life Power Application", Abs. 23, IMLB 12 Meeting (1 page).

New Li$_4$Ti$_5$O$_{12}$ Anode Material of Süd-Chemie AG for Lithium Ion Batteries, Süd-Chemie EXM 1037—Li$_4$Ti$_5$O$_{12}$, Product Specification (2 pages).

"Battery Materials—Ceramic Anode Material for 2.4 V Lithium-Ion Batteries"—EXM 1037—Li$_4$Ti$_5$O$_{12}$ (1 page), available at least by Oct. 25, 2004.

Guerfi, et. al., "Nano Electronically Conductive Titanium-Spinel as Lithium Ion Storage Negative Electrode", Journal of Power Sources, 126, 2004, pp. 163-168.

Prosini, et. al., "Li$_4$Ti$_5$O$_{12}$ As Anode In All-Solid-State, Plastic, Lithium-Ion Batteries for Low-Power Applications" Solid State Ionics, 144, 2001, pp. 185-192.

Scrosati, "Low Voltage Lithium-Ion Cells", Advances in Lithium-Ion Batteries Kluwer Academic/Plenum Publishers, pp. 289-308.

Nakahara, et al. "Preparation of Particulate Li$_4$Ti$_5$O$_{12}$ Having Excellent Characteristics As An Electrode Active Material For Power Storage Cells", Journal of Power Sources, 117, 2003, pp. 131-136.

Medtronic Neurostimulation Systems Product Brochure, Copyright 2002 Medtronic, Inc. (6 pages).

Medtronic Activa® Product Family and Procedure Solution Product Specifications, Copyright 2003 Medtronic, Inc. (6 pages).

Preliminary Amendment for U.S. Appl. No. 10/979,040, filed with the USPTO on Mar. 4, 2005, 11 pages.

Office Action for U.S. Appl. No. 10/979,040, dated Apr. 2, 2008, 8 pages.

Reply and Amendment and Declaration Under 1.131 for U.S. Appl. No. 10/979,040, filed with the USPTO on Jul. 16, 2008, 33 pages.

Dahn et al., "Combinatorial Study of Sn1-xCox (0<x<0.6) and [5n0.55Co0.45]1-yCy (0<y<0.5) Alloy Negative Electrode Materials for Li-Ion Batteries," Journal of Electrochemical Society, vol. 153, 2006, pp. A361-A365.

Fauteux et al., "Rechargeable lithium battery anodes: alternatives to metallic lithium," Journal of Applied Electrochemistry, vol. 23, 1993, pp. 1-10.

Guyomard et al., "New amorphous oxides as high capacity negative electrodes for lithium6 batteries the LixMV04 (M=Ni, Co, Cd, Zn; 1<x<8) series," Journal of Power Sources, vol. 68, 1997, pp. 692-697.

Linden, David, Editor in Chief, Handbook of Batteries, Second Edition, McGraw-Hill, NY, 1995, 6 pages.

Ohzuku et al., "Why transition metal (di)oxides are the most attractive materials for batteries," Solid State Ionics, vol. 69, 1994, pp. 201-211.

Poizot et al., "Nano-sized transition-metal oxides as negative-electrode materials for lithium-ion batteries," Nature, vol. 407, 2000, cover and pp. 496-499.

Trifonova et al., "Sn-Sb and Sn-Bi Alloys as Anode Materials for Lithium-Ion Batteries," Ionics, vol. 8, 2002, cover and pp. 321-328.

Winter et al., "Insertion Electrode Materials for Rechargeable Lithium Batteries," Advanced Materials, vol. 10, 1998, pp. 725-763.

Winter et al., "Electrochemical lithiation of tin and tin-based intermetallics and composites," Electrochimica Acta, vol. 45, 1999, pp. 31-50.

Final Office Action for U.S. Appl. No. 10/979,040, dated Sep. 19, 2008, 10 pages.

Request for Continued Examination (RCE) and Reply and Amendment for U.S. Appl. No. 10/979,040, filed with the USPTO on Dec. 11, 2008, 16 pages.

U.S. Appl. No. 12/112,979, filed Apr. 30, 2008, Scott et al.

U.S. Appl. No. 12/240,652, filed Sep. 29, 2008, Scott et al.

International Search Report and Written Opinion for Application No. PCT/US2008/066809, mailing date Oct. 29, 2008, 8 pages.

International Search Report and Written Opinion for Application No. PCT/US2008/066801, mailing date Oct. 29, 2008, 10 pages.

International Search Report and Written Opinion for Application No. PCT/US2008/066803, date of mailing Oct. 7, 2008, 12 pages.

International Search Report and Written Opinion for Application No. PCT/US2008/082598, date of mailing Feb. 18, 2009, 11 pages.

Non-Final Office Action for U.S. Appl. No. 10/979,040, dated Jan. 12, 2009, 10 pages.

Non-Final Office Action for U.S. Appl. No. 11/260,853, dated Mar. 5, 2009, 13 pages.

Reply and Amendment for U.S. Appl. No. 10/979,040, filed Aug. 14, 2009, 13 pages.

Notice of Allowance for U.S. Appl. No. 11/260,853, dated Aug. 5, 2009, 7 pages.

Final Office Action for U.S. Appl. No. 10/979,040, dated Jun. 16, 2009, 10 pages.

Amendment and Reply for U.S. Appl. No. 11/260,853, filed Jun. 4, 2009, 14 pages.

Belharouak et al., "On the Safety of the Li$_4$Ti$_5$O$_{12}$/LiMn$_2$O$_4$ Lithium-Ion Battery System," (ECS) *Journal of The Electrochemical Society*, 2007, pp. A1083-A1087, vol. 154, No. 12.

Christensen et al., "Optimization of Lithium Titanate Electrodes for High-Power Cells," (ECS) *Journal of The Electrochemical Society*, 2006, pp. A560-A565, vol. 153, No. 3.

Sun et al., "The Compatibility of a Boron-Based Anion Receptor with the Carbon Anode in Lithium-Ion Batteries," (ECS) *Electrochemical and Solid-State Letters*, 2003, pp. A43-A46, vol. 6, No. 2.

Sun et al., "Using a Boron-Based Anion Receptor Additive to Improve the Thermal Stability of LiPF$_6$-Based Electrolyte for Lithium Batteries," (ECS) *Electrochemical and Solid-State Letters*, 2002, pp. A248-A251, vol. 5, No. 11.

Non-Final Office Action for U.S. Appl. No. 10/979,040, dated Sep. 30, 2009, 7 pages.

Request for Continued Examination for U.S. Appl. No. 10/979,040, filed Sep. 11, 2009, 3 pages.

Advisory Action for U.S. Appl. No. 10/979,040, dated Aug. 24, 2009, 3 pages.

Reply and Amendment for U.S. Appl. No. 10/979,040, filed Aug. 17, 2009, 13 pages.

Reply and Amendment for U.S. Appl. No. 10/979,040, filed Mar. 24, 2009, 12 pages.

* cited by examiner

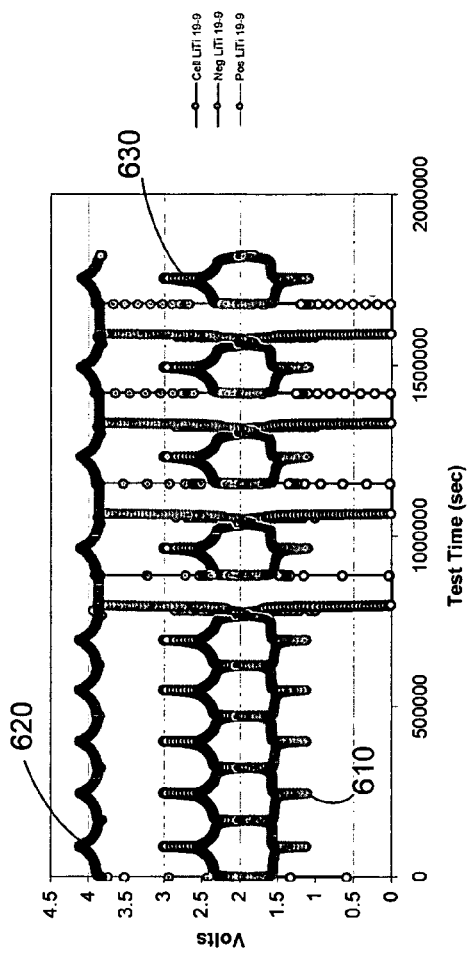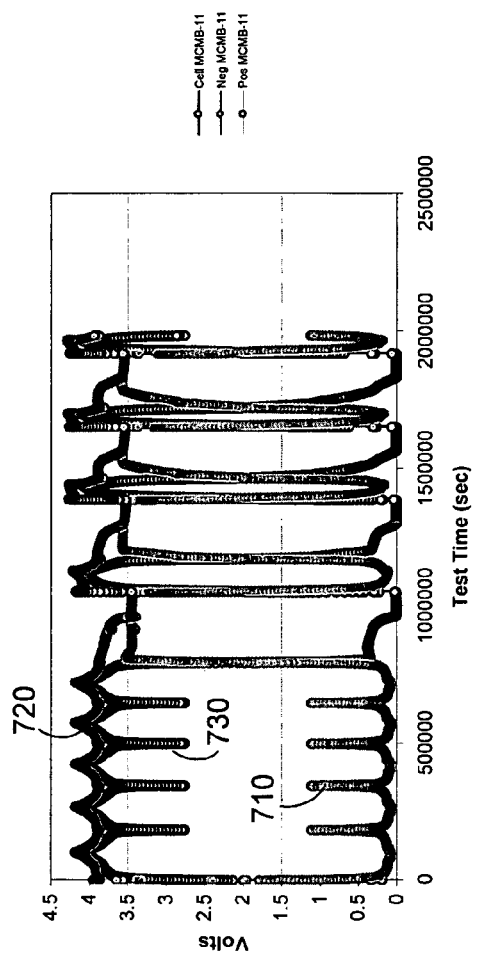
FIGURE 6
FIGURE 7

MEDICAL DEVICE HAVING LITHIUM-ION BATTERY

BACKGROUND

The present invention relates generally to the field of lithium-ion batteries. Specifically, the present invention relates to lithium-ion batteries that are relatively tolerant to over-discharge conditions.

Lithium-ion batteries include a positive current collector (e.g., aluminum such as an aluminum foil) having an active material provided thereon (e.g., $LiCoO_2$) and a negative current collector (e.g., copper such as a copper foil) having an active material (e.g., a carbonaceous material such as graphite) provided thereon. Together the positive current collector and the active material provided thereon are referred to as a positive electrode, while the negative current collector and the active material provided thereon are referred to as a negative electrode.

FIG. 1 shows a schematic representation of a portion of a lithium-ion battery 10 such as that described above. The battery 10 includes a positive electrode 20 that includes a positive current collector 22 and a positive active material 24, a negative electrode 30 that includes a negative current collector 32 and a negative active material 34, an electrolyte material 40, and a separator (e.g., a polymeric microporous separator, not shown) provided intermediate or between the positive electrode 20 and the negative electrode 30. The electrodes 20, 30 may be provided as relatively flat or planar plates or may be wrapped or wound in a spiral or other configuration (e.g., an oval configuration). The electrode may also be provided in a folded configuration.

During charging and discharging of the battery 10, lithium ions move between the positive electrode 20 and the negative electrode 30. For example, when the battery 10 is discharged, lithium ions flow from the negative electrode 30 to the to the positive electrode 20. In contrast, when the battery 10 is charged, lithium ions flow from the positive electrode 20 to the negative electrode 30.

FIG. 2 is a graph 100 illustrating the theoretical charging and discharging behavior for a conventional lithium-ion battery. Curve 110 represents the electrode potential versus a lithium reference electrode for a positive electrode that includes an aluminum current collector having a $LiCoO_2$ active material provided thereon, while curve 120 represents the electrode potential versus a lithium reference electrode for a negative electrode that includes a copper current collector having a carbonaceous active material provided thereon. The difference between curves 110 and 120 is representative of the overall cell voltage.

As shown in FIG. 2, upon initial charging to full capacity, the potential of the positive electrode, as shown by curve 110, increases from approximately 3.0 volts to a point above the corrosion potential of copper used to form the negative electrode (designated by dashed line 122). The potential of the negative electrode decreases from approximately 3.0 volts to a point below the decomposition potential of the $LiCoO_2$ active material provided on the aluminum current collector (designated by dashed line 112). Upon initial charging, the battery experiences an irreversible loss of capacity due to the formation of a passive layer on the negative current collector, which may be referred to as a solid-electrolyte interface ("SEI"). The irreversible loss of capacity is shown as a ledge or shelf 124 in curve 120.

One difficulty with conventional lithium-ion batteries is that when such a battery is discharged to a point near zero volts, it may exhibit a loss of deliverable capacity and corrosion of the negative electrode current collector (copper) and possibly of the battery case, depending on the material used and the polarity of the case. As shown in FIG. 2, after initial charging of the battery, a subsequent discharge of the battery in which the voltage of the battery approaches zero volts (i.e., zero percent capacity) results in a negative electrode potential that follows a path designated by dashed line 126. As shown in FIG. 2, the negative electrode potential levels off or plateaus at the copper corrosion potential of the negative current collector (approximately 3.5 volts for copper and designated by dashed line 122 in FIG. 2).

The point at which the curves 110 and 120 cross is sometimes referred to as the zero voltage crossing potential, and corresponds to a cell voltage that is equal to zero (i.e., the difference between the two curves equals zero at this point). Because of the degradation of the copper current collector which occurs at the copper corrosion potential, the copper material used for the negative current collector corrodes before the cell reaches a zero voltage condition, resulting in a battery that exhibits a loss of deliverable capacity.

While FIG. 2 shows the theoretical charging and discharging behavior of a battery that may experience corrosion of the negative current collector when the battery approaches a zero voltage configuration, it should be noted that there may also be cases in which the active material on the positive current collector may degrade in near-zero-voltage conditions. In such cases, the theoretical charging and discharging potential of the positive electrode versus a lithium reference electrode would decrease to the decomposition potential of the positive active material (shown as line 112 in FIG. 2), at which point the positive active material would decompose, resulting in potentially decreased protection against future over-discharge conditions.

Because damage to the lithium-ion battery may occur in the event of a low voltage condition, conventional lithium-ion batteries may include protection circuitry and/or may be utilized in devices that include protection circuitry which substantially reduces the current drain from the battery (e.g., by disconnecting the battery).

The medical device industry produces a wide variety of electronic and mechanical devices for treating patient medical conditions. Depending upon the medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life.

It may be desirable to provide a source of battery power for such medical devices, including implantable medical devices. In such cases, it may be advantageous to provide a battery that may be recharged. It may also be advantageous to provide a battery that may be discharged to a near zero voltage condition without substantial risk that the battery may be damaged (e.g., without corroding one of the electrodes or the battery case, decomposing the positive active material, etc.) such that the performance of the battery is degraded in subsequent charging and discharging operations.

It would be advantageous to provide a battery (e.g., a lithium-ion battery) that may be discharged to near zero volts without producing a subsequent decrease in the amount of deliverable capacity or producing a corroded negative electrode or battery case. It would also be advantageous to provide a battery that compensates for the irreversible loss of capacity resulting from initial charging of the battery to allow the battery to be used in near zero voltage conditions without significant degradation to battery performance. It would also be advantageous to provide a medical device (e.g., an implantable medical device) that utilizes a battery that includes any one or more of these or other advantageous features.

SUMMARY

An exemplary embodiment relates to a medical device that includes a rechargeable lithium-ion battery for providing power to the medical device. The lithium-ion battery includes a positive electrode comprising a current collector and an active material comprising a material selected from the group consisting of $LiCoO_2$, $LiMn_2O_4$, $LiNi_xCo_yMn_{(1-x-y)}O_2$, $LiAl_xCo_yNi_{(1-x-y)}O_2$, $LiTi_xCo_yNi_{(1-x-y)}O_2$ and combinations thereof. The lithium-ion battery also includes a negative electrode having a current collector and an active material including a lithium titanate material. The current collector of the negative electrode includes a material selected from the group consisting of aluminum, titanium, and silver. The battery is configured for cycling to near-zero-voltage conditions without a substantial loss of battery capacity.

Another exemplary embodiment relates to a device for providing at least one of a therapeutic treatment and a diagnostic function to a patient. The device includes a rechargeable battery for providing power to the device. The battery includes a positive electrode having a current collector and an active material selected from the group consisting of $LiCoO_2$, $LiMn_2O_4$, $LiNi_xCo_yMn_{(1-x-y)}O_2$, $LiAl_xCo_yNi_{(1-x-y)}O_2$, $LiTi_xCo_yNi_{(1-x-y)}O_2$, and combinations thereof. The battery also includes a negative electrode comprising a negative current collector and an active material provided on the negative current collector. The negative current collector includes aluminum and the active material provided on the negative current collector comprising a lithium titanate material.

Another exemplary embodiment relates to a system for providing at least one of a therapeutic treatment and a diagnostic function to a patient. The system includes a lithium-ion battery configured to provide power to the system and being capable of being charged and discharged. The lithium-ion battery includes a positive electrode having an aluminum current collector and an active material provided in contact with the aluminum current collector and comprising a material selected from the group consisting of $LiCoO_2$, $LiMn_2O_4$, $LiNi_xCo_yMn_{(1-x-y)}O_2$, $LiAl_xCo_yNi_{(1-x-y)}O_2$, $LiTi_xCo_yNi_{(1-x-y)}O_2$, and combinations thereof. The lithium-ion battery also includes a negative electrode comprising an aluminum current collector and an active material. The active material provided on the current collector of the negative electrode includes $Li_4Ti_5O_{12}$. The positive electrode and the negative electrode have a zero voltage crossing potential above a decomposition potential of the $LiCoO_2$ active material.

Another exemplary embodiment relates to a method of treating a medical condition of a patient. The method includes providing at least a portion of a medical device in contact with the patient and providing power to the medical device from a battery such that the medical device provides a therapeutic treatment to the patient. The battery includes a positive electrode having a current collector and an active material selected from the group consisting of $LiCoO_2$, $LiMn_2O_4$, $LiNi_xCo_yMn_{(1-x-y)}O_2$, $LiAl_xCo_yNi_{(1-x-y)}O_2$, $LiTi_xCo_yNi_{(1-x-y)}O_2$, and combinations thereof. The battery also includes a negative electrode having a negative current collector and an active material provided on the negative current collector. The negative current collector includes aluminum and the active material provided on the negative current collector comprising a lithium titanate material.

BRIEF DESCRIPTION OF THE DRAWINGS

FIG. 6 is a graph illustrating voltage traces for a cell using a Li4Ti5O12 active material on an aluminum negative current collector.

FIG. 7 is a graph illustrating voltage traces for a comparative cell using a carbon active material on a copper negative current collector.

DETAILED DESCRIPTION OF THE EXEMPLARY EMBODIMENTS

Figure 3:
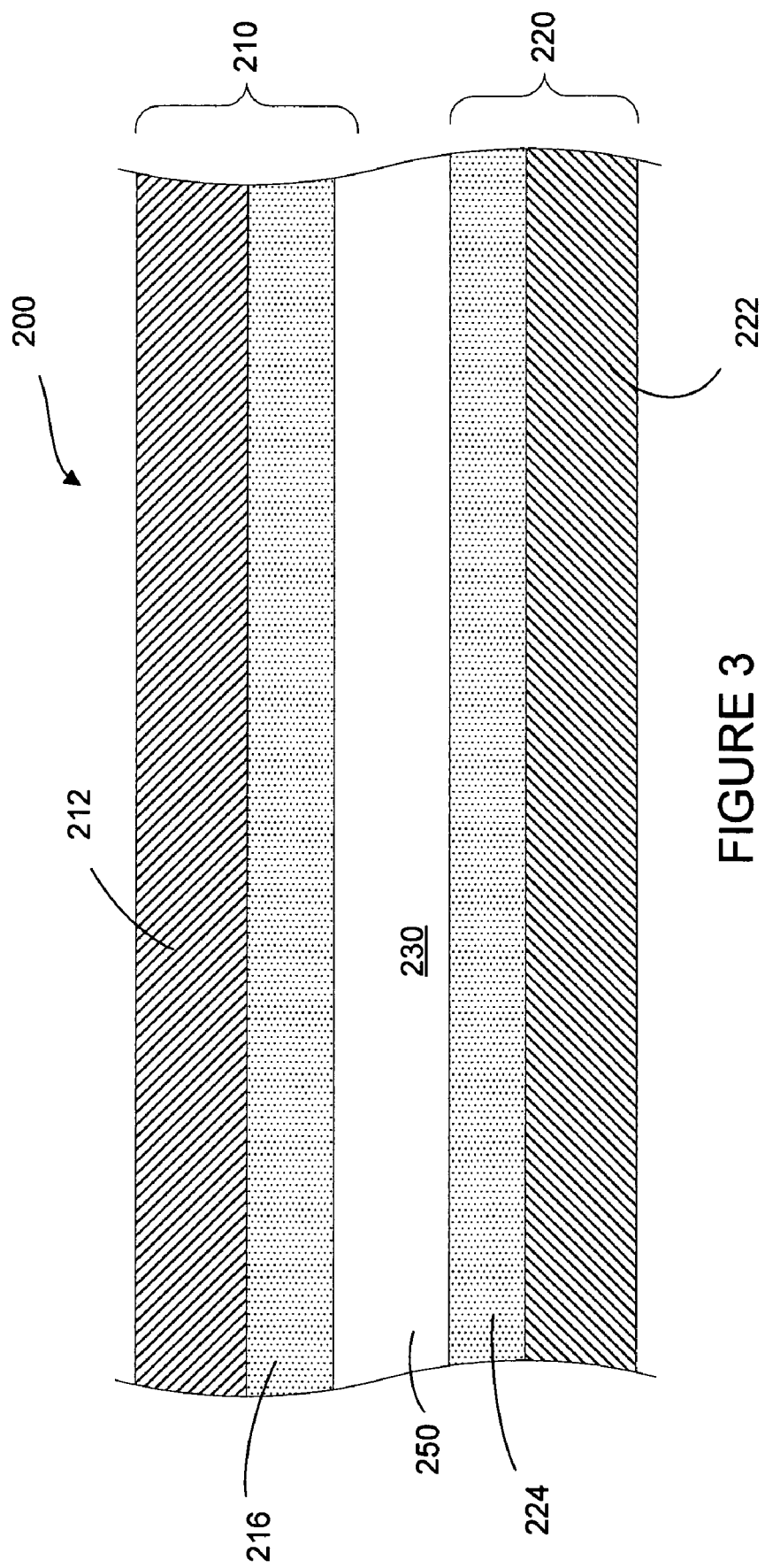
FIG. 3 is a schematic cross-sectional view of a portion of a lithium-ion battery according to an exemplary embodiment.

With reference to FIG. 3, a schematic cross-sectional view of a portion of a lithium-ion battery 200 is shown according to an exemplary embodiment. According to an exemplary embodiment, the battery 200 has a rating of between approximately 10 and 1000 milliampere hours (mAh). According to another exemplary embodiment, the battery has a rating of between approximately 100 and 400 mAh. According to another exemplary embodiment, the battery is an approximately 300 mAh battery. According to another exemplary embodiment, the battery is an approximately 75 mAh battery.

The battery 200 includes at least one positive electrode 210 and at least one negative electrode 220. The electrodes may be provided as flat or planar components of the battery 200, may be wound in a spiral or other configuration, or may be provided in a folded configuration. For example, the electrodes may be wrapped around a relatively rectangular mandrel such that they form an oval wound coil for insertion into a relatively prismatic battery case. According to other exemplary embodiments, the battery may be provided as a button cell battery, a thin film solid state battery, or as another lithium-ion battery configuration.

The battery case (not shown) may be made of a metal such as aluminum or an aluminum alloy or another metal. According to an exemplary embodiment, the battery case may be made of titanium, a titanium alloy, or stainless steel. According to another exemplary embodiment, the battery case may be made of a plastic material or a plastic-foil laminate material (e.g., an aluminum foil provided intermediate a polyolefin layer and a polyester layer).

According to an exemplary embodiment, the negative electrode is coupled to an aluminum case by a member or tab comprising aluminum or an aluminum alloy. An aluminum or aluminum alloy member or tab may be coupled or attached to the positive electrode. The tabs may serve as terminals for the battery according to an exemplary embodiment.

The dimensions of the battery 200 may differ according to a variety of exemplary embodiments. For example, according to one exemplary embodiment in which the electrodes are wound such that they may be provided in a relatively prismatic battery case, the battery has dimensions of between approximately 30-40 mm by between approximately 20-30 mm by between approximately 5-7 mm. According to another exemplary embodiment, the dimensions of the battery are approximately 20 mm by 20 mm by 3 mm. According to another exemplary embodiment, a battery may be provided in the form of a button cell type battery having a diameter of approximately 30 mm and a thickness of approximately 3 mm. It will be appreciated by those of skill in the art that such dimensions and configurations as are described herein are illustrative only, and that batteries in a wide variety of sizes, shapes, and configurations may be produced in accordance with the novel concepts described herein.

An electrolyte 230 is provided intermediate or between the positive and negative electrodes to provide a medium through which lithium ions may travel. The electrolyte may be a liquid (e.g., a lithium salt dissolved in one or more non-aqueous solvents). According to an exemplary embodiment, the electrolyte may be a mixture of polycarbonate (PC) and a 1.0 M salt of $LiPF_6$. According to another exemplary embodiment, an electrolyte may be used that is free of ethylene carbonate, vinylene carbonate or a lithium bis-oxalatoborate salt (sometimes referred to as LiBOB) that may be used in conventional lithium batteries.

Various other electrolytes may be used according to other exemplary embodiments. According to an exemplary embodiment, the electrolyte may be a lithium salt dissolved in a polymeric material such as poly(ethylene oxide) or silicone. According to another exemplary embodiment, the electrolyte may be an ionic liquid such as N-methyl-N-alkylpyrrolidinium bis(trifluoromethanesulfonyl)imide salts. According to another exemplary embodiment, the electrolyte may be a solid state electrolyte such as a lithium-ion conducting glass such as lithium phosphorous oxynitride (LiPON). According to another exemplary embodiment, the electrolyte may be a 1:1 mixture of ethylene carbonate to diethylene carbonate (EC:DEC) in a 1.0 M salt of $LiPF_6$. According to another exemplary embodiment, the electrolyte may include a polypropylene carbonate solvent and a lithium bis-oxalatoborate salt. According to other exemplary embodiments, the electrolyte may comprise one or more of a PVDF copolymer, a PVDF-polyimide material, and organosilicon polymer, a thermal polymerization gel, a radiation cured acrylate, a particulate with polymer gel, an inorganic gel polymer electrolyte, an inorganic gel-polymer electrolyte, a PVDF gel, polyethylene oxide (PEO), a glass ceramic electrolyte, phosphate glasses, lithium conducting glasses, lithium conducting ceramics, and an inorganic ionic liquid gel, among others.

A separator 250 is provided intermediate or between the positive electrode 210 and the negative electrode 220. According to an exemplary embodiment, the separator 250 is a polymeric material such as a polypropylene/polyethelene copolymer or another polyolefin multilayer laminate that includes micropores formed therein to allow electrolyte and lithium ions to flow from one side of the separator to the other. The thickness of the separator 250 is between approximately 10 micrometers ($\mu$m) and 50 $\mu$m according to an exemplary embodiment. According to a particular exemplary embodiment, the thickness of the separator is approximately 25 $\mu$m and the average pore size of the separator is between approximately 0.02 $\mu$m and 0.1 $\mu$m.

The positive electrode 210 includes a current collector 212 made of a conductive material such as a metal. According to an exemplary embodiment, the current collector 212 comprises aluminum or an aluminum alloy.

According to an exemplary embodiment, the thickness of the current collector 212 is between approximately 5 $\mu$m and 75 $\mu$m. According to a particular exemplary embodiment, the thickness of the current collector 212 is approximately 20 $\mu$m. It should also be noted that while the positive current collector 212 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

The current collector 212 has a layer of active material 216 provided thereon (e.g., coated on the current collector). While FIG. 3 shows that the active material 216 is provided on only one side of the current collector 212, it should be understood that a layer of active material similar or identical to that shown as active material 216 may be provided or coated on both sides of the current collector 212.

According to an exemplary embodiment, the active material 216 is a material or compound that includes lithium. The lithium included in the primary active material 216 may be doped and undoped during discharging and charging of the battery, respectively. According to an exemplary embodiment, the primary active material 216 is lithium cobalt oxide ($LiCoO_2$). According to another exemplary embodiment, the active material provided on the current collector 212 is $LiMn_2O_4$. According to another exemplary embodiment, the active material provided on the current collector 212 is a material of the form $LiCo_xNi_{(1-x)}O_2$, where x is between approximately 0.05 and 0.8. According to another exemplary embodiment, the active material provided on the current collector 212 is a material of the form $LiNi_xCo_yMn_{(1-x-y)}O_2$ (e.g., $LiNi_{1/3}Co_{1/3}Mn_{1/3}O_2$). According to another exemplary embodiment, the active material provided on the current collector 212 is a metal-doped variety of one of these materials, such as a material of the form $LiM_xCo_yNi_{(1-x-y)}O_2$, where M is aluminum or titanium and x is between approximately 0.05 and 0.3 and y is between approximately 0.1 and 0.3.

For certain applications, it may be desirable to provide a battery having a cell voltage of greater than approximately 3 volts. In such cases, a higher-voltage active material may be utilized on the positive current collector, such as a material in the form $Li_{2-x}Co_yFe_zMn_{4-(y+z)}O_8$ (e.g., $Li_2Co_{0.4}Fe_{0.4}Mn_{3.2}O_8$). It is believed that such an active material may charge up to 5.2 volts versus a lithium reference electrode, making it possible to obtain an overall cell voltage of up to approximately 3.7 volts. Other relatively high-voltage active materials that may be used for the positive electrode include $LiCoPO_4$; $Li_2CoPO_4F$; $LiNiPO_4$; $Li[Ni_{0.2}Li_{0.2}Mn_{0.6}]O_2$; and $LiCo_xMn_{2-x}O_4$ (e.g., $LiCo_{0.3}Mn_{1.7}O_4$).

According to various other exemplary embodiments, the active material may include a material such as a material of the form $Li_{1-x}MO_2$ where M is a metal (e.g., $LiCoO_2$, $LiNiO_2$, and $LiMnO_2$), a material of the form $Li_{1-w}(M'_xM''_y)O_2$ where M' and M" are different metals (e.g., $Li(Cr_xMn_{1-x})O_2$, $Li(Al_xMn_{1-x})O_2$, $Li(Co_xM_{1-x})O_2$ where M is a metal, $Li(Co_xNi_{1-x})O_2$, and $Li(Co_xFe_{1-x})O_2$)), a material of the form $Li_{1-w}(Mn_xNi_yCo_z)O_2$ (e.g., $Li(Mn_{1/3}Ni_{1/3}Co_{1/3})O_2$, $Li(Mn_{1/3}Ni_{1/3}Co_{1/3-x}Mg_x)O_2$, $Li(Mn_{0.4}Ni_{0.4}Co_{0.2})O_2$, and $Li(Mn_{0.1}Ni_{0.1}Co_{0.8})O_2$), a material of the form $Li_{1-w}(Mn_xNi_xCo_{1-2x})O_2$, a material of the form $Li_{1-w}(Mn_xNi_yCo_zAl_w)O_2$, a material of the form $Li_{1-w}(Ni_xCo_yAl_z)O_2$ (e.g., $Li(Ni_{0.8}Co_{0.15}Al_{0.05})O_2$), a material of the form $Li_{1-w}(Ni_xCo_yM_z)O_2$ where M is a metal, a material of the form $Li_{1-w}(Ni_xMn_yM_z)O_2$ where M is a metal, a material of the form Li(Ni$_{x-y}$Mn$_y$Cr$_{2-x}$)O$_4$, LiMn$_2$O$_4$, a material of the form LiM'M''$_2$O$_4$ where M' and M'' are different metals (e.g., LiMn$_{2-y-z}$Ni$_y$O$_4$, Li$_z$O$_4$, LiMn$_{1.5}$Ni$_{0.5}$O$_4$, LiNiCuO$_4$, LiMn$_{1-x}$Al$_x$O$_4$, LiNi$_{0.5}$Ti$_{0.5}$O$_4$, and Li$_{1.05}$Al$_{0.1}$Mn$_{1.85}$O$_{4-z}$F$_z$), Li$_2$MnO$_3$, a material of the form Li$_x$V$_y$O$_z$ (e.g., LiV$_3$O$_8$, LiV$_2$O$_5$, and LiV$_6$O$_{13}$), a material of the form LiMPO$_4$ where M is a metal or LiM$_x$'M''$_{1-x}$PO$_4$ where M' and M'' are different metals (e.g., LiFePO$_4$, LiFe$_x$M$_{1-x}$PO$_4$ where M is a metal, LiVOPO$_4$, and Li$_3$V$_2$(PO$_4$)$_3$, and LiMPO$_{4x}$ where M is a metal such as iron or vanadium and X is a halogen such as fluorine, and combinations thereof.

A binder material may also be utilized in conjunction with the layer of active material 216 to bond or hold the various electrode components together. For example, according to an exemplary embodiment, the layer of active material may include a conductive additive such as carbon black and a binder such as polyvinylidine fluoride (PVDF) or an elastomeric polymer.

According to an exemplary embodiment, the thickness of the layer of active material 216 is between approximately 0.1 μm and 3 mm. According to another exemplary embodiment, the thickness of the layer of active material 216 is between approximately 25 μm and 300 μm. According to a particular exemplary embodiment, the thickness of the layer of active material 216 is approximately 75 μm.

The negative electrode 220 includes a current collector 222 that is made of a conductive material such as a metal. According to an exemplary embodiment, the current collector 222 is aluminum or an aluminum alloy. One advantageous feature of utilizing an aluminum or aluminum alloy current collector is that such a material is relatively inexpensive and may be relatively easily formed into a current collector. Other advantageous features of utilizing an aluminum or aluminum current collector is that such a material may exhibit a relatively low density, a relatively high conductivity, is relatively readily weldable, and is generally commercially available. According to another exemplary embodiment, the current collector 222 is titanium or a titanium alloy. According to another exemplary embodiment, the current collector 222 is silver or a silver alloy.

While the negative current collector 222 has been illustrated and described as being a thin foil material, the negative current collector may have any of a variety of other configurations according to various exemplary embodiments. For example, the positive current collector may be a grid such as a mesh grid, an expanded metal grid, a photochemically etched grid, or the like.

According to an exemplary embodiment, the thickness of the current collector 222 is between approximately 100 nm and 100 μm. According to another exemplary embodiment, the thickness of the current collector 222 is between approximately 5 μm and 25 μm. According to a particular exemplary embodiment, the thickness of the current collector 222 is approximately 10 μm.

The negative current collector 222 has an active material 224 provided thereon. While FIG. 3 shows that the active material 224 is provided on only one side of the current collector 222, it should be understood that a layer of active material similar or identical to that shown may be provided or coated on both sides of the current collector 222.

According to an exemplary embodiment, the negative active material 224 is a lithium titanate material such as Li$_4$Ti$_5$O$_{12}$ (sometimes referred to as Li$_{1+x}$[Li$_{1/3}$Ti$_{5/3}$]O$_4$, with 0≦x<1). Other lithium titanate materials which may be suitable for use as the negative active material may include one or more of the following lithium titanate spinel materials: H$_x$Li$_{y-x}$TiO$_x$O$_4$, H$_x$Li$_{y-x}$TiO$_x$O$_4$, Li$_4$M$_x$Ti$_{5-x}$O$_{12}$, Li$_x$Ti$_y$O$_4$, Li$_x$Ti$_y$O$_4$, Li$_4$[Ti$_{1.67}$Li$_{0.33-y}$M$_y$]O$_4$, Li$_2$TiO$_3$, Li$_4$Ti$_{4.75}$V$_{0.25}$O$_{12}$, Li$_4$Ti$_{4.75}$Fe$_{0.25}$O$_{11.88}$, Li$_4$Ti$_{4.5}$Mn$_{0.5}$O$_{12}$, and LiM'M''XO$_4$ (where M' is a metal such as nickel, cobalt, iron, manganese, vanadium, copper, chromium, molybdenum, niobium, or combinations thereof, M'' is an optional three valent non-transition metal, and X is zirconium, titanium, or a combination of these two). Note that such lithium titanate spinel materials may be used in any state of lithiation (e.g., Li$_{4+x}$Ti$_5$O$_{12}$, where 0≦x≦3).

A binder material may also be utilized in conjunction with the layer of active material 224. For example, according to an exemplary embodiment, the layer of active material may include a binder such as polyvinylidine fluoride (PVDF) or an elastomeric polymer. The active material 224 may also include a conductive material such as carbon (e.g., carbon black) at weight loadings of between zero and ten percent to provide increased electronic conductivity.

According to various exemplary embodiments, the thickness of the active material 224 is between approximately 0.1 μm and 3 mm. According to other exemplary embodiments, the thickness of the active material 224 may be between approximately 25 μm and 300 μm. According to another exemplary embodiment, the thickness of the active material 224 may be between approximately 20 μm and 90 μm, and according to a particular exemplary embodiment, approximately 75 μm.

Figure 4:
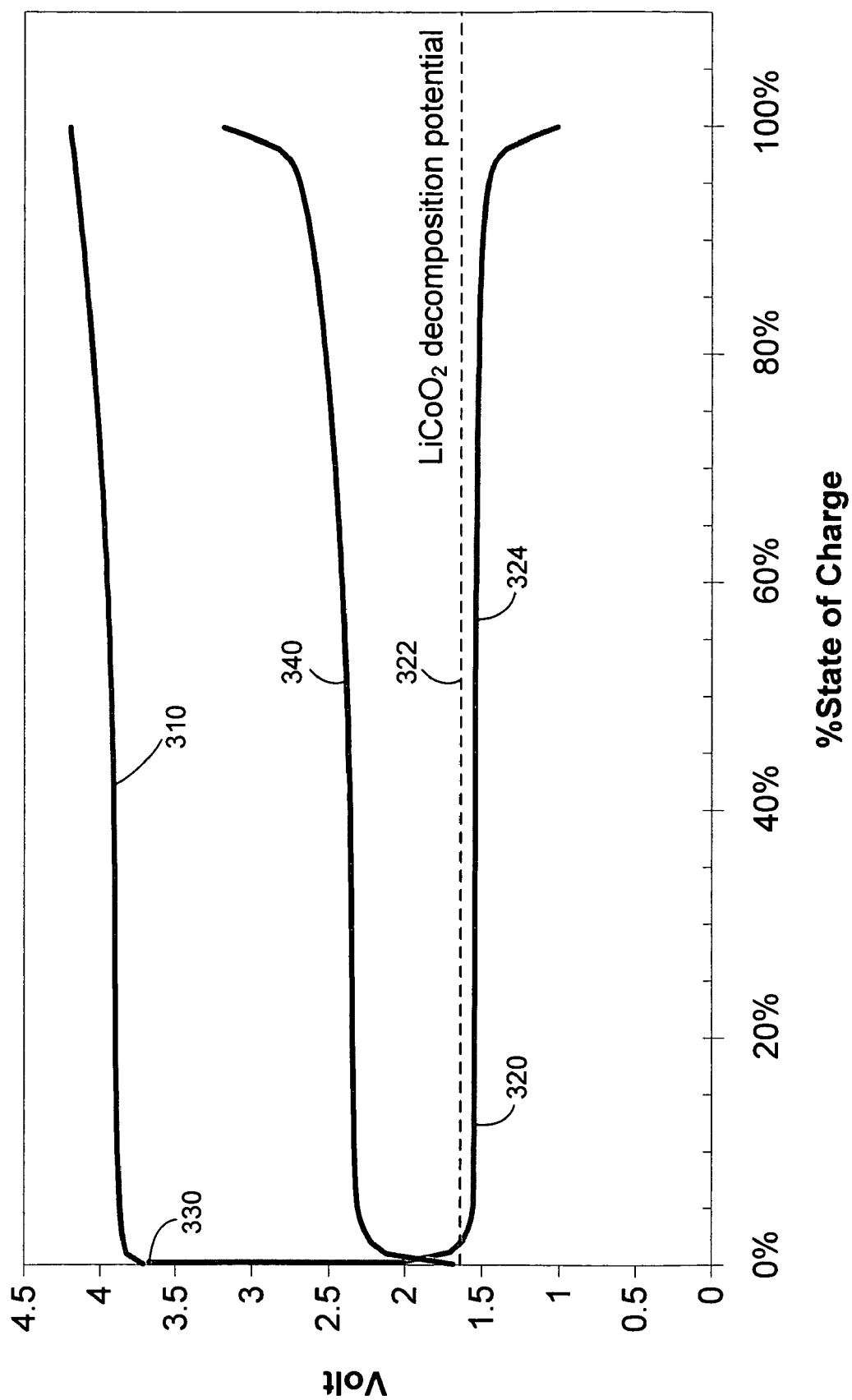
FIG. 4 is a graph illustrating the theoretical charging and discharging behavior for a lithium-ion battery such as that shown in FIG. 3.

FIG. 4 is a graph 300 illustrating the theoretical charging and discharging behavior for a lithium-ion battery constructed in accordance with an exemplary embodiment such as that shown and described with regard to FIG. 3. Curve 310 represents the electrode potential versus a lithium reference electrode for a positive electrode (e.g., positive electrode 210) that includes an aluminum current collector having a LiCoO$_2$ primary active material provided thereon.

Curve 320 represents the electrode potential versus a lithium reference electrode for a negative electrode that includes an aluminum current collector having a lithium titanate active material provided thereon. The difference between curves 310 and 320 is representative of the overall cell voltage of the battery, and is represented as curve 340 in FIG. 4.

Figure 1:
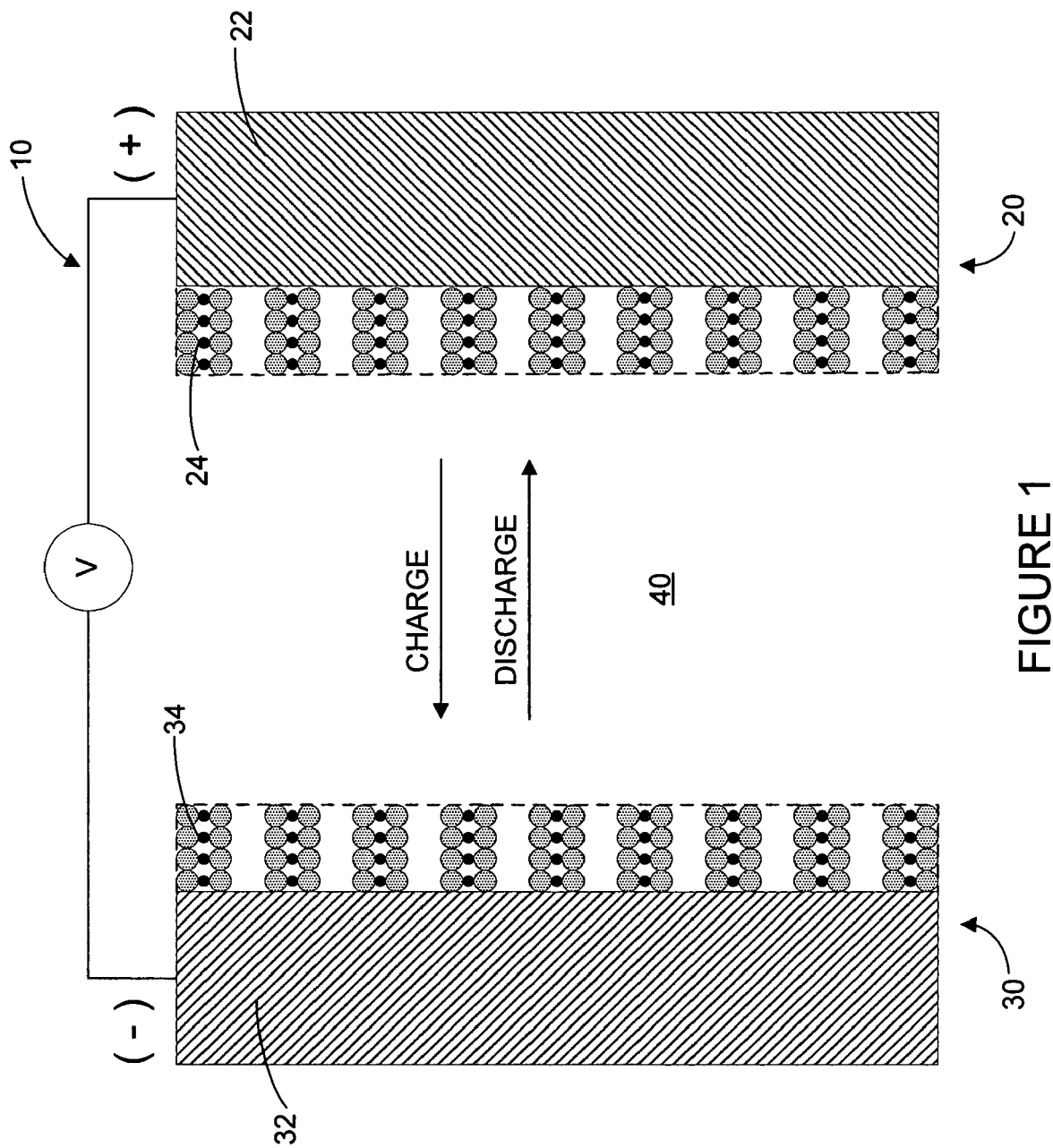
FIG. 1 is a schematic cross-sectional view of a conventional lithium-ion battery.
Figure 2:
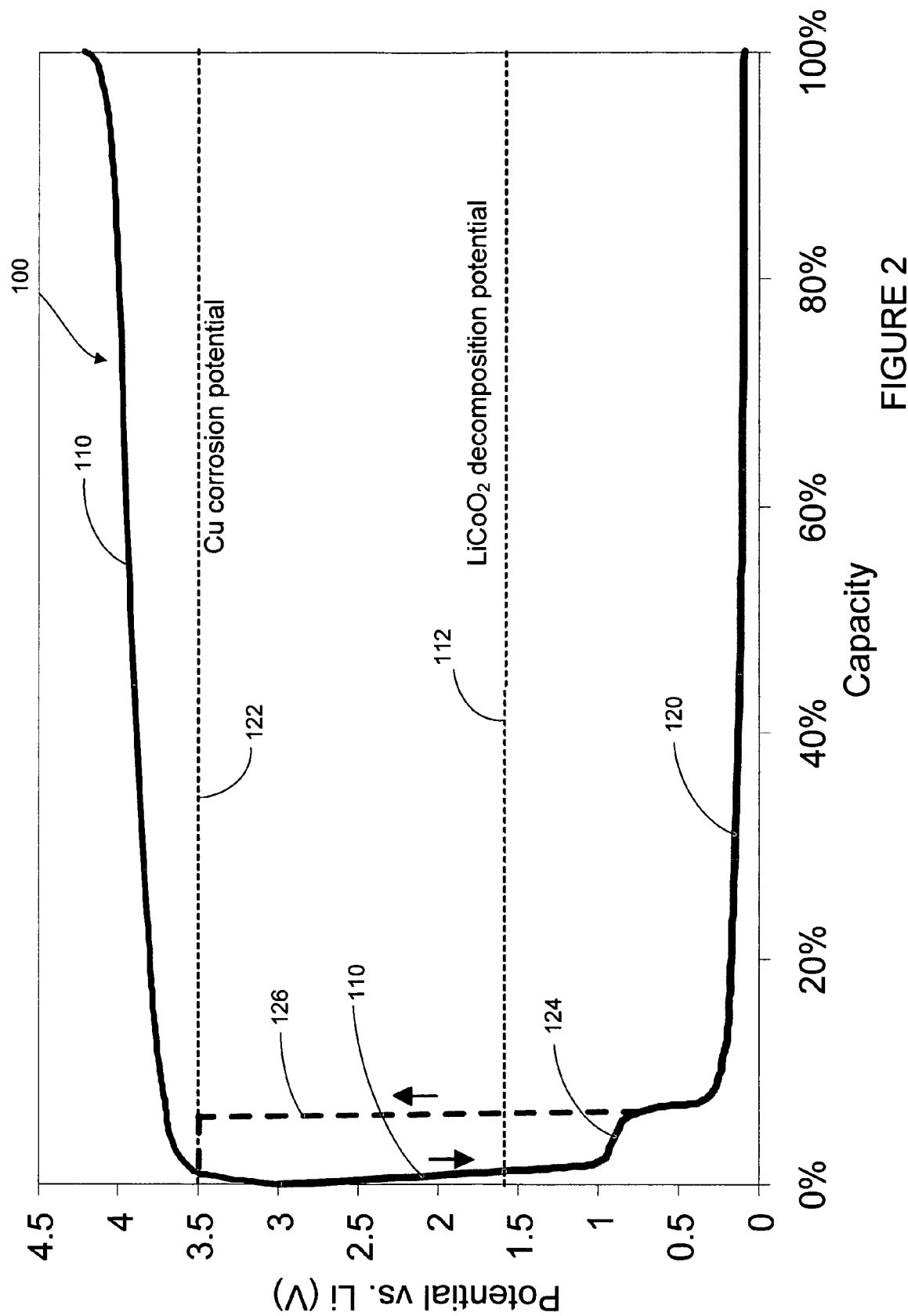
FIG. 2 is a graph illustrating the theoretical charging and discharging behavior for a conventional lithium-ion battery such as that shown schematically in FIG. 1.

As shown in FIG. 4, the relatively flat portion (labeled with reference numeral 324) of the curve 320 representing the voltage of the negative electrode (e.g., electrode 220) is at a level of between approximately 1.5 and 1.6 volts. Thus, the relatively flat portion 324 of the curve 320 is at a level that is significantly greater than that of an electrode utilizing a carbon active material (see, e.g., curve 120 in FIG. 2, which represents the theoretical voltage versus a lithium reference electrode for a negative electrode incorporating a carbon active material).

When the cell is charged, the potentials of the positive and negative electrodes progress to the right along curves 310 and 320, respectively. When the cell is discharged, the potentials of the positive and negative electrode potentials progress toward the left along curves 310 and 320, respectively, with a zero voltage crossing potential of approximately 3.8 volts (shown as point 330 in FIG. 4). As the cell approaches a zero voltage condition (e.g., curve 340 drops to zero volts, representing the voltage differential between the positive and negative electrodes), the voltage of the positive electrode is above the decomposition potential of the LiCoO$_2$ active material provided thereon, which is shown as dashed line 322 in FIG. 4. Additionally, because an aluminum current collector is utilized for the negative electrode, the negative electrode has increased resistance to corrosion as compared to copper materials which may be utilized for the negative electrode.

It is intended that a lithium-ion battery such as that described herein may be fully discharged while the materials for both electrodes, including their corresponding current collectors, are stable (e.g., corrosion of the current collectors and/or the decomposition of active material may be avoided, etc.). For example, it is intended that a battery produced using a positive electrode including an aluminum current collector and a $LiCoO_2$ active material and a negative electrode including an aluminum current collector and a lithium titanate active material will allow for repeated cycling of the battery to zero or near-zero voltage conditions without a significant decline in battery charging capacity or battery performance. One potential advantageous feature of such an arrangement is that the occurrence of reduced device functionality (i.e., the need to recharge more frequently) and corrosion of the current collectors and battery case (with the incumbent possibility of leaking potentially corrosive and toxic battery contents) may be reduced or avoided.

Various advantageous features may be obtained by batteries such as those shown and described herein. For example, use of batteries which utilize a lithium titanate active material on an aluminum electrode may eliminate the need to utilize circuitry to disconnect batteries approaching near-zero voltage conditions, since such batteries may be cycled to zero voltage and near-zero voltage repeatedly without a significant loss in battery performance or capacity. By not utilizing circuitry for this function, volume and cost reductions may be obtained.

One advantageous feature of using a lithium titanate material is that it is believed that when used in a negative electrode of a lithium-ion battery, such materials will cycle lithium at a potential plateau of about 1.55 volts versus a lithium reference electrode. This is substantially higher than graphitic carbon, which cycles lithium at approximately 0.1 volts in the fully charged state (see, e.g., FIG. 2, in which curve 120 is representative of the charging/discharging behavior of a negative electrode utilizing graphitic carbon). As a result, the battery using lithium titanate is believed to be less likely to result in plating of lithium (which occurs at 0 volts versus a lithium reference) while being charged. Lithium plating is a well-known phenomenon that can lead to loss in performance of lithium ion batteries.

Another advantage of using a lithium titanate material instead of a carbonaceous material for the negative active material is that it is believed that the use of a lithium titanate material allows for charging and discharging of the battery at higher rates than is capable using carbonaceous materials. For example, a common upper limit for the rate of charge in lithium ion batteries is about 1 C (meaning that the battery can be fully charged from the discharged state in one hour). Conversely, it has been reported in literature that lithium titanate may be charged at rates up to 10 C (i.e., attaining full charge in $\frac{1}{10}$ hour, or six minutes). One potential reason for this is that negative electrodes utilizing a lithium titanate active material are believed to be less susceptible to the risk of lithium plating. The ability to recharge a battery more quickly may substantially increase the functionality of devices that employ such a battery.

It is also believed that the use of negative electrodes that include a lithium titanate active material may allow for charging of the battery at voltages that exceed those used in the charging of batteries in which the negative electrodes utilize carbon active materials. One potential advantage of such a property is that nonhermetic cells (e.g., cells using a rivet polymer feedthrough, foil package, etc.) may be produced. Nonhermetic cells typically have greater energy density than other cells, are relatively inexpensive to manufacture, and may be produced using a wider variety of materials (e.g., polymer foil laminates, etc.). In medical applications in particular, such cells have conventionally utilized with polymer or gel electrolytes which have lower vapor pressure to provide a reduced risk of leakage. However, such electrolytes are typically less conductive than liquid electrolytes, resulting in relatively low power and/or charge rate. By utilizing a battery that includes a lithium titanate active material on an aluminum current collector, the charge voltage of the cell may be increased to compensate for resistive losses (e.g., IR drops) in the electrolyte.

Lithium titanate materials are also believed to offer superior cycle life because they are so called "zero-strain" materials. Zero strain materials have crystal lattices which do not experience shrinkage or contraction with lithium doping/de-doping, making them free from strain-related degradation mechanisms. Such materials also have a relatively high specific capacity (approximately 155 mAh/g) and a similar volumetric capacity density to graphitic carbon.

A further advantage of the higher potential of the lithium titanate material is that it avoids decomposition of organic solvents (such as propylene carbonate) commonly used in lithium ion batteries. In so doing, it may reduce negative consequences such as formation of gas, cell swelling, and reduction of reversible battery capacity.

Another potential advantageous feature of utilizing a lithium titanate material for the negative electrode active material is that more favorable design rules may be possible. For example, in conventional lithium-ion cells, the negative electrode must overlap the positive electrode by approximately 1 mm on all edges in order to avoid plating of lithium. For applications in which space is a concern, this may result in significant wasted volume (e.g., for a cranial implant cell that is approximately 22 mm high, this may result in wasted volume of approximately 10 percent). Because use of a titanate material reduces the risk of lithium plating, it is believed that the design requirement of overlapping positive and negative electrodes may be unnecessary, thus allowing the production of lithium-ion batteries with improved energy density.

The lithium diffusion coefficient for lithium titanate materials may be on the order of approximately $2 \times 10^{-8}$ cm$^2$/s, which is approximately ten times that of carbon, thus allowing a comparatively rapid sustained rate capability. The use of such materials may allow the manufacture of batteries having lower surface area electrodes while still achieving adequate power and recharge rates. According to an exemplary embodiment, a battery utilizes monolithic (i.e., single-plate) electrodes in a coin cell or a foil laminate package. Due to the comparatively rapid sustained rate capability of the lithium titanate material, the battery may be relatively thin (e.g., approximately 1 mm) and inexpensive. Further, according to other exemplary embodiments, batteries may be produced in contoured shapes, which may allow for packaging of such batteries unobtrusively and in unconventional ways in a device (such as along an inner surface of a device housing or case, such as the housing or case of a medical device such as a pacemaker). This may be especially advantageous in a device such as a cranial implant, where it may be desirable to provide the device having a contour to match the curvature of the skull.

Conventional lithium-ion cells are balanced with a nominal excess negative active material of between approximately five and ten percent to avoid plating of lithium. The use of excess active material results in a larger battery, which results in a cell having reduced energy density. According to an exemplary embodiment, a battery or cell using a lithium titanate active material on an aluminum negative current collector may be produced without excess negative active material (e.g., as a "balanced design").

COMPARATIVE EXAMPLE #1

This example illustrates the overdischarge performance of lithium ion batteries utilizing a negative electrode having $Li_4Ti_5O_{12}$ active material coated onto an aluminum current collector as compared to the performance of lithium ion batteries in which a carbon active material (graphitized MCMB) is coated onto a copper current collector. In all cases, the electrodes were cycled against positive electrodes having a $LiCoO_2$ active material with a capacity of 5.53 mAh coated on an aluminum current collector.

Negative electrodes were produced by mixing lithium titanate (commercially available from Süd Chemie Corporation) with a poly(vinylidine fluoride) binder, carbon black and 1-methyl-2-pyrolidone (NMP) into a slurry and depositing the mixture onto an aluminum foil current collector and drying on a heated drum. The active weight percent of the dried coating was 89.25%. Three coating deposition levels of the coating were used: 17.37, 18.78 and 20.69 mg/cm². Based on the theoretical specific capacity of $Li_4Ti_5O_{12}$ (155 mAh/g), the capacity of these electrodes was 4.76, 5.14 and 5.67 mAh, respectively. Thus, when cycled against the positive electrodes, the cell balance (i.e., the ratio of the negative and positive electrode capacities) was 0.85, 0.93 and 1.02, respectively.

After drying, the electrode coatings were calendared to a density of about 2.2 g/cm³ and cut into circular disks having an area of 1.98 cm². Lithium ion cells were produced by assembling these electrodes into type-2032 coin cell hardware. A microporous polyolefin separator was used to separate the negative and positive electrodes, and the cells were activated by the addition of electrolyte consisting of 1 M $LiPF_6$ in a mixture of propylene carbonate, ethylene carbonate and diethyl carbonate.

Comparative cells were manufactured in identical fashion, with the exception of the fact that the negative electrodes utilized graphite active material (mesocarbon microbeads) coated on copper foil.

Cells were charged and discharged at a rate of 0.2 mA using an ARBIN BT2000 battery cycler. For the first four cycles, the cells were cycled over a normal operating voltage range (3.0 to 1.8 V for the $Li_4Ti_5O_{12}$ cells, 4.075 to 2.75 volts for the comparative cells). After completing four cycles, the cells then underwent four overdischarge cycles, where they were discharged to 0 volts and charged back to their normal charge voltage. The overdischarge took place as a sequence of steps at progressively lower currents: 0.2 mA down to 1.8 volts, 0.05 mA to 1.0 volts and 0.01 mA to 0 volts. Following the overdischarge cycles, the cells were then cycled over the original voltage range to measure the recovered capacity for the cells.

Figure 5:
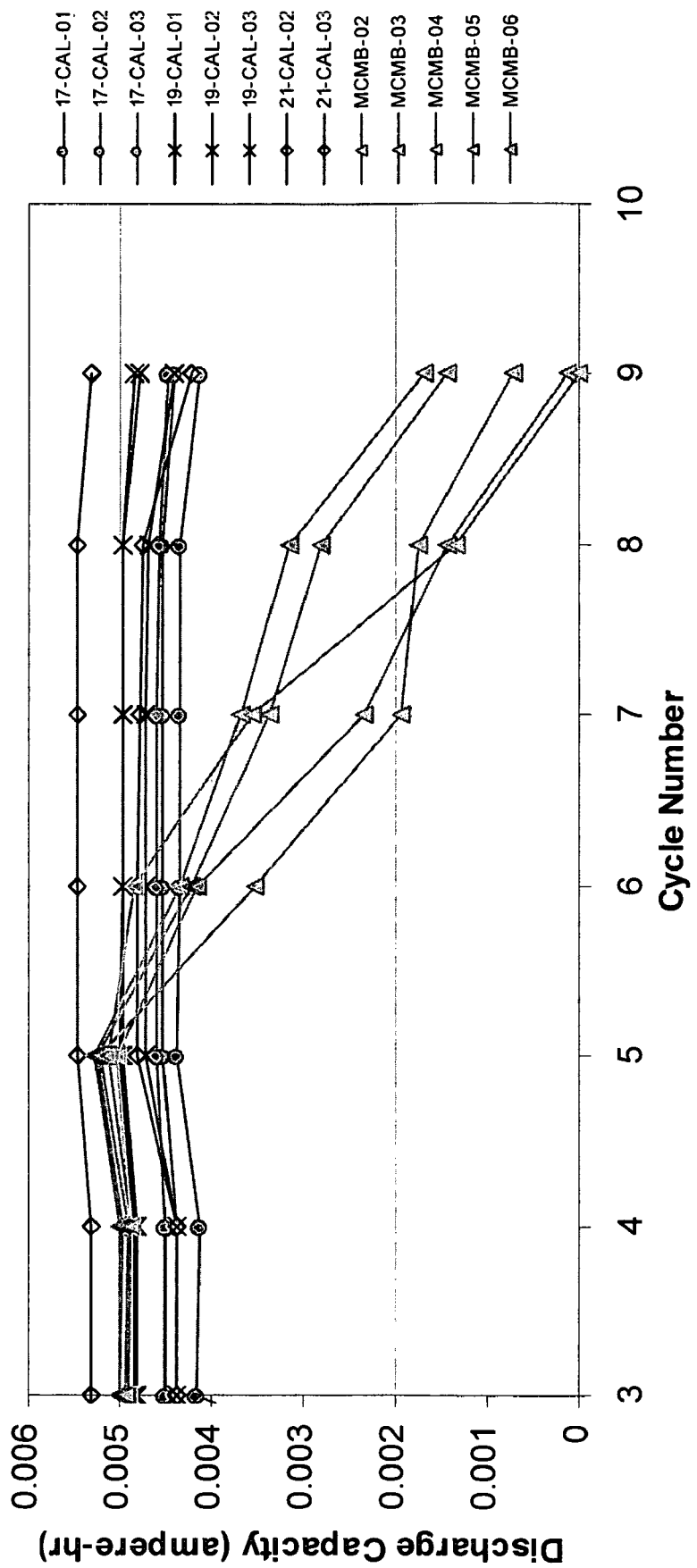
FIG. 5 is a graph illustrating the discharge capacity of battery cells and the effect of overdischarge cycling of such cells.

A graph showing the discharge capacity versus cycle number for each of the cells tested is shown in FIG. 5. Test data revealed a loss of discharge capacity over time after repeated overdischarge cycling for the comparative cells (i.e., cells using carbon active material on copper current collectors), while little or no loss of discharge capacity was observed for cells utilizing $Li_4Ti_5O_{12}$ negative active material and an aluminum foil current collector.

TABLE 1 lists the cell discharge capacity of the cells during the fourth and ninth cycles of testing (i.e., the cycles immediately preceding and immediately following the overdischarge cycles). For cells using negative electrodes with a $Li_4Ti_5O_{12}$ active material on an aluminum current collector, there is little or no loss in capacity following the overdischarge cycles. For the comparative cells (graphite active material on copper current collector), the average capacity loss was observed to be 84%.

TABLE 1 also lists the ratio of theoretical capacity of the negative and positive electrodes for the $Li_4Ti_5O_{12}$ cells. This data indicates that little or no capacity loss may be obtained regardless of whether the cells are negative limited (ratio of negative to positive electrode capacity less than 1) or positive limited (ratio of negative to positive electrode capacity greater than 1).

TABLE 1

| Group/Serial Number | Negative Active Material | Negative/Positive Electrode Capacity Ratio for $Li_4Ti_5O_{12}$ Cells | Cycle 4 Discharge Capacity (mAh) | Cycle 9 Discharge Capacity (mAh) | Capacity Loss Due to Overdischarge |
|---|---|---|---|---|---|
| 17-CAL-01 | $Li_4Ti_5O_{12}$ | 0.86 | 4.12 | 4.13 | −0.3% |
| 17-CAL-02 | $Li_4Ti_5O_{12}$ | 0.86 | 4.37 | 4.40 | −0.6% |
| 17-CAL-03 | $Li_4Ti_5O_{12}$ | 0.86 | 4.49 | 4.47 | 0.4% |
|  |  | Average | 4.33 | 4.33 | −0.2% |
|  |  | Standard Dev. | 0.19 | 0.18 | 0.5% |
| 19-CAL-01 | $Li_4Ti_5O_{12}$ | 0.93 | 4.81 | 4.83 | −0.4% |
| 19-CAL-02 | $Li_4Ti_5O_{12}$ | 0.93 | 4.36 | 4.40 | −0.8% |
| 19-CAL-03 | $Li_4Ti_5O_{12}$ | 0.93 | 4.84 | 4.78 | 1.2% |
|  |  | Average | 4.67 | 4.67 | 0.0% |
|  |  | Standard Dev. | 0.27 | 0.24 | 1.1% |
| 21-CAL-02 | $Li_4Ti_5O_{12}$ | 1.02 | 5.32 | 5.32 | 0.1% |
| 21-CAL-03 | $Li_4Ti_5O_{12}$ | 1.02 | 4.37 | 4.23 | 3.2% |
|  |  | Average | 4.84 | 4.77 | 1.6% |
|  |  | Standard Dev. | 0.67 | 0.77 | 2.2% |
| MCMB-02 | Carbon | n/a | 4.99 | 1.68 | 66.4% |
| MCMB-03 | Carbon | n/a | 4.96 | 1.44 | 71.0% |
| MCMB-04 | Carbon | n/a | 4.88 | 0.14 | 97.1% |
| MCMB-05 | Carbon | n/a | 4.91 | 0.72 | 85.3% |
| MCMB-06 | Carbon | n/a | 4.88 | 0.00 | 100.0% |
|  |  | Average | 4.93 | 0.80 | 84.0% |
|  |  | Standard Dev. | 0.05 | 0.75 | 15.1% |

COMPARATIVE EXAMPLE #2

This example illustrates potential advantageous features of utilizing a $Li_4Ti_5O_{12}$ active material on a negative current collector made of aluminum as opposed to a negative current collector made of copper. In all cases described below, the negative electrodes were cycled against positive electrodes having a $LiCoO_2$ active material having a capacity of 14.1 mAh.

A negative electrode was produced by mixing lithium titanate (commercially available from Süd Chemie Corporation) with poly(vinylidine fluride) binder, carbon black and 1-methyl-2-pyrolidone (NMP) into a slurry and depositing the slurry onto an aluminum foil current collector and drying on a heated drum. The active weight percent of the dried coating was 89.25%. The coating deposition level was 18.78 mg/cm². The active area of the electrode was 5.04 cm². Based on the theoretical specific capacity of $Li_4Ti_5O_{12}$ (155 mAh/g), the capacity of this electrode was 13.1 mAh.

A battery was assembled by combining the above-mentioned negative and positive electrodes, spaced by a microporous separator, inside if a hermetic stainless steel can. The negative electrode was welded onto the inside of the can, and the positive electrode was connected to a an electrical feedthrough. A lithium reference electrode was placed on the end of a second feedthrough pin, such that the lithium was located in the headspace of the cell. A polyolefin spacer was placed inside the can, parallel to the positive electrodes, to maintain uniform contact across the entire electrode surface. The cell was activated by filling with electrolyte consisting of 1 M $LiPF_6$ in a mixture of propylene carbonate, ethylene carbonate and diethyl carbonate.

The battery was cycled by charging and discharging at a current of 0.5 mA using an ARBIN BT2000 battery cycler. For the first four cycles, the cell was cycled over a typical operational voltage range (charge to 3.0 volts, discharge to 1.8 volts). Next, the cell was subjected to four overdischarge steps consisting of a normal charge followed by overdischarge to 0 volts. The overdischarge took place as a sequence of galvanostatic steps, as follows: 0.5 mA down to 1.8 volts, 0.125 mA down to 1.0 volts, 0.05 mA down to 0 volts. After the overdischarge steps, the cell was again charged and discharged per the original method. An auxiliary voltage measuring channel was used to record the potential of the negative electrode versus the lithium reference electrode. The potential of the positive electrode was obtained by summing the total battery voltage with the auxiliary voltage.

FIG. 6 shows three voltage traces for the cell. Curve 630 is the total cell voltage, curve 620 is the positive electrode (versus Li reference) and curve 610 is the negative electrode (versus Li reference). During normal cycling, the potential of the negative electrode ranges between about 1.2 and 2.1 volts. However, during overdischarge, the potential of the negative electrode increases until it meets the potential of the positive electrode. The two electrodes meet at a potential of approximately 3.9 volts. At this point, known as the "zero-volt crossing potential," the cell voltage (defined as the difference between the positive and negative electrode potentials) is 0 volts. If this cell were to have been made using a copper current collector for the negative electrodes, it is expected that the copper would have corroded, because 3.9 volts is several hundred millivolts more anodic than the corrosion potential of copper (approximately 3.5 volts).

A battery was fabricated and tested using methods identical to those described above. The battery utilized a negative electrode including a graphitized carbon active material on a copper current collector. FIG. 7 shows the voltage traces for this battery (i.e., curve 710 is the total cell voltage, curve 720 is the positive electrode (versus Li reference) and curve 730 is the negative electrode (versus Li reference)). During the overdischarge cycle, the potential of the negative electrode was never above approximately 3.5 volts. It is believed that the reason for this is that at this point, the copper current collector was freely corroding, with the driving force for the corrosion reaction being supplied by the positive electrode.

According to an exemplary embodiment, lithium-ion batteries such as those described above may be used in conjunction with medical devices such as medical devices that may be implanted in the human body (referred to as "implantable medical devices" or "IMD's").

Figure 8:
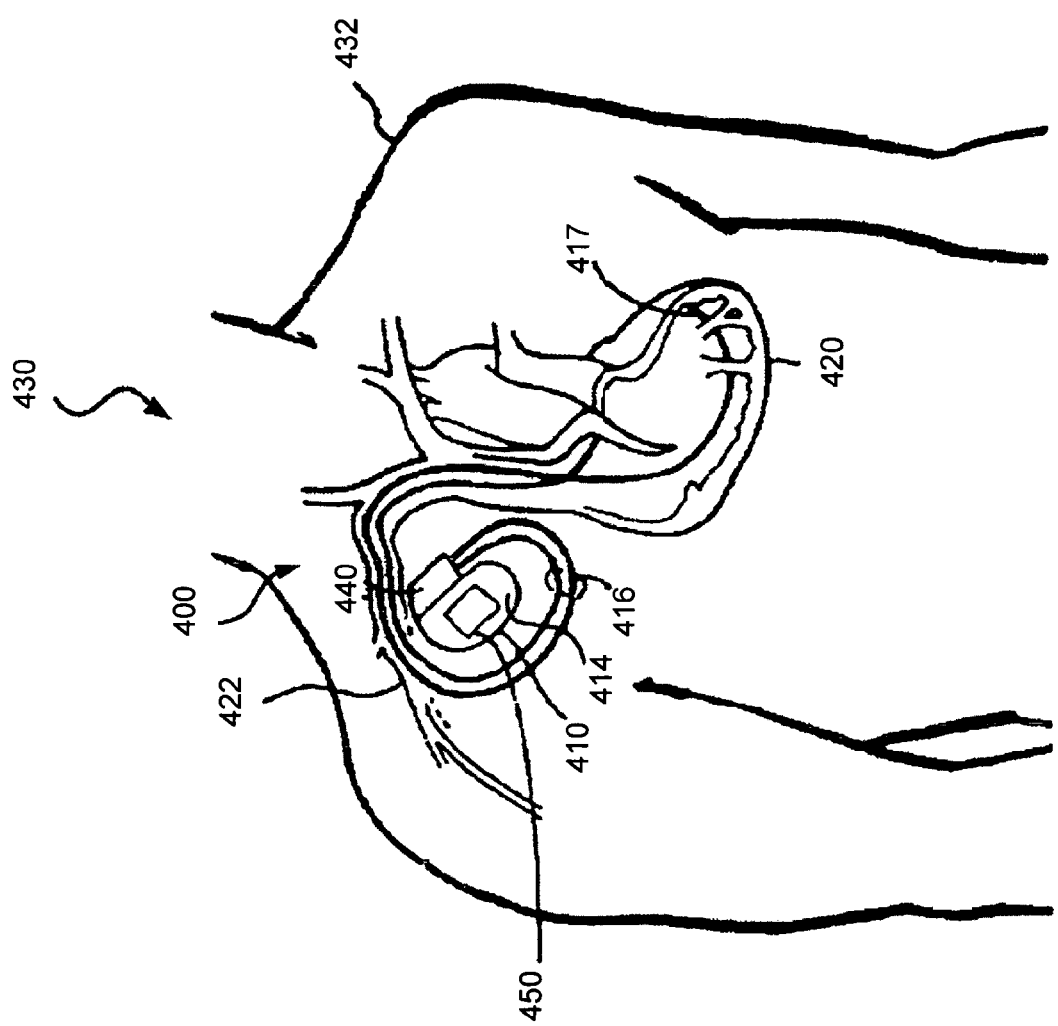
FIG. 8 is a schematic view of a system in the form of an implantable medical device implanted within a body or torso of a patient.

FIG. 8 illustrates a schematic view of a system 400 (e.g., an implantable medical device) implanted within a body or torso 432 of a patient 430. The system 400 includes a device 410 in the form of an implantable medical device that for purposes of illustration is shown as a defibrillator configured to provide a therapeutic high voltage (e.g., 700 volt) treatment for the patient 430.

The device 410 includes a container or housing 414 that is hermetically sealed and biologically inert according to an exemplary embodiment. The container may be made of a conductive material. One or more leads 416 electrically connect the device 410 and to the patient's heart 420 via a vein 422. Electrodes 417 are provided to sense cardiac activity and/or provide an electrical potential to the heart 420. At least a portion of the leads 416 (e.g., an end portion of the leads shown as exposed electrodes 417) may be provided adjacent or in contact with one or more of a ventricle and an atrium of the heart 420.

The device 410 includes a battery 440 provided therein to provide power for the device 410. According to another exemplary embodiment, the battery 440 may be provided external to the device or external to the patient 430 (e.g., to allow for removal and replacement and/or charging of the battery). The size and capacity of the battery 440 may be chosen based on a number of factors, including the amount of charge required for a given patient's physical or medical characteristics, the size or configuration of the device, and any of a variety of other factors. According to an exemplary embodiment, the battery is a 5 mAh battery. According to another exemplary embodiment, the battery is a 300 mAh battery. According to various other exemplary embodiments, the battery may have a capacity of between approximately 10 and 1000 mAh.

According to other exemplary embodiments, more than one battery may be provided to power the device 410. In such exemplary embodiments, the batteries may have the same capacity or one or more of the batteries may have a higher or lower capacity than the other battery or batteries. For example, according to an exemplary embodiment, one of the batteries may have a capacity of approximately 500 mAh while another of the batteries may have a capacity of approximately 75 mAh.

Figure 9:
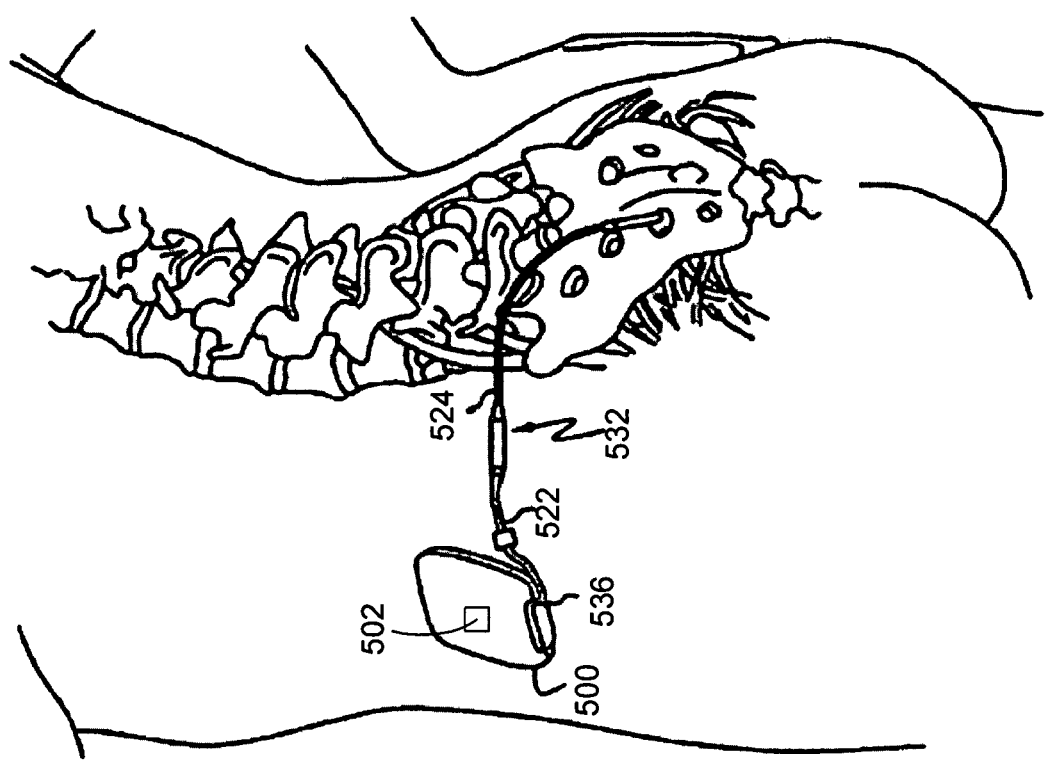
FIG. 9 is schematic view of another system in the form of an implantable medical device.

According to another exemplary embodiment shown in FIG. 9, an implantable neurological stimulation device 500 (an implantable neuro stimulator or INS) may include a battery 502 such as those described above with respect to the various exemplary embodiments. Examples of some neuro stimulation products and related components are shown and described in a brochure titled "Implantable Neurostimulation Systems" available from Medtronic, Inc.

An INS generates one or more electrical stimulation signals that are used to influence the human nervous system or organs. Electrical contacts carried on the distal end of a lead are placed at the desired stimulation site such as the spine or brain and the proximal end of the lead is connected to the INS.

The INS is then surgically implanted into an individual such as into a subcutaneous pocket in the abdomen, pectoral region, or upper buttocks area. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions. Before an INS is implanted to deliver a therapy, an external screener that replicates some or all of the INS functions is typically connected to the patient to evaluate the efficacy of the proposed therapy.

The INS 500 includes a lead extension 522 and a stimulation lead 524. The stimulation lead 524 is one or more insulated electrical conductors with a connector 532 on the proximal end and electrical contacts (not shown) on the distal end. Some stimulation leads are designed to be inserted into a patient percutaneously, such as the Model 3487A Pisces-Quad® lead available from Medtronic, Inc. of Minneapolis Minn., and stimulation some leads are designed to be surgically implanted, such as the Model 3998 Specify® lead also available from Medtronic.

Although the lead connector 532 can be connected directly to the INS 500 (e.g., at a point 536), typically the lead connector 532 is connected to a lead extension 522. The lead extension 522, such as a Model 7495 available from Medtronic, is then connected to the INS 500.

Implantation of an INS 520 typically begins with implantation of at least one stimulation lead 524, usually while the patient is under a local anesthetic. The stimulation lead 524 can either be percutaneously or surgically implanted. Once the stimulation lead 524 has been implanted and positioned, the stimulation lead's 524 distal end is typically anchored into position to minimize movement of the stimulation lead 524 after implantation. The stimulation lead's 524 proximal end can be configured to connect to a lead extension 522.

The INS 500 is programmed with a therapy and the therapy is often modified to optimize the therapy for the patient (i.e., the INS may be programmed with a plurality of programs or therapies such that an appropriate therapy may be administered in a given situation). In the event that the battery 502 requires recharging, an external lead (not shown) may be used to electrically couple the battery to a charging device or apparatus.

A physician programmer and a patient programmer (not shown) may also be provided to allow a physician or a patient to control the administration of various therapies. A physician programmer, also known as a console programmer, uses telemetry to communicate with the implanted INS 500, so a clinician can program and manage a patient's therapy stored in the INS 500, troubleshoot the patient's INS 500 system, and/or collect data. An example of a physician programmer is a Model 7432 Console Programmer available from Medtronic. A patient programmer also uses telemetry to communicate with the INS 500, so the patient can manage some aspects of her therapy as defined by the clinician. An example of a patient programmer is a Model 7434 Itrel® 3 EZ Patient Programmer available from Medtronic.

While the medical devices described herein (e.g., systems 400 and 500) are shown and described as a defibrillator and a neurological stimulation device, it should be appreciated that other types of implantable medical devices may be utilized according to other exemplary embodiments, such as pacemakers, cardioverters, cardiac contractility modules, drug administering devices, diagnostic recorders, cochlear implants, and the like for alleviating the adverse effects of various health ailments. According to still other embodiments, non-implantable medical devices or other types of devices may utilize batteries as are shown and described in this disclosure.

It is also contemplated that the medical devices described herein may be charged or recharged when the medical device is implanted within a patient. That is, according to an exemplary embodiment, there is no need to disconnect or remove the medical device from the patient in order to charge or recharge the medical device. For example, transcutaneous energy transfer (TET) may be used, in which magnetic induction is used to deliver energy from outside the body to the implanted battery, without the need to make direct physical contact to the implanted battery, and without the need for any portion of the implant to protrude from the patient's skin. According to another exemplary embodiment, a connector may be provided external to the patient's body that may be electrically coupled to a charging device in order to charge or recharge the battery. According to other exemplary embodiments, medical devices may be provided that may require removal or detachment from the patient in order to charge or recharge the battery.

It is important to note that the construction and arrangement of the lithium-ion battery as shown and described with respect to the various exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. Accordingly, all such modifications are intended to be included within the scope of the present invention as defined in the appended claims. Other substitutions, modifications, changes and omissions may be made in the design, operating conditions and arrangement of the preferred and other exemplary embodiments without departing from the scope of the present invention as expressed in the appended claims.

What is claimed is:

1. A medical device comprising:
   a rechargeable lithium-ion battery for providing power to the medical device, the lithium-ion battery comprising:
   a positive electrode comprising a current collector and an active material comprising a material selected from the group consisting of $LiCoO_2$, $LiMn_2O_4$, $LiNi_{1/3}Co_{1/3}Mn_{1/3}O_2$, $LiAl_xCo_yNi_{(1-x-y)}O_2$ where x is between approximately 0.05 and 0.3 and y is between approximately 0.1 and 0.3, $LiTi_xCo_yNi_{(1-x-y)}O_2$ where x is between approximately 0.05 and 0.3 and y is between approximately 0.1 and 0.3, and combinations thereof;
   a negative electrode comprising a foil current collector and an active material comprising a lithium titanate material, the current collector of the negative electrode comprising a material selected from the group consisting of aluminum, titanium, and combinations thereof;
   a liquid electrolyte; and
   a polymeric separator provided intermediate the positive electrode and the negative electrode that includes pores for allowing the liquid electrolyte to flow through the separator;
   whereby the battery is configured for cycling to near-zero-voltage conditions without a substantial loss of battery capacity.

2. The medical device of claim 1, wherein at least a portion of the medical device is configured for implantation into a body of a patient.

3. The medical device of claim 2, wherein a portion of the medical device including the lithium-ion battery is implanted within the body of the patient and wherein the lithium-ion battery may be charged without removing the lithium-ion battery from the body of the patient.

4. The medical device of claim 1, wherein the medical device comprises a neurological stimulation device.

5. The medical device of claim 4, wherein the neurological stimulation device is configured to provide a therapeutic treatment to a patient by electrically stimulating a portion of at least one of a patient's brain and a patient's spine.

6. The medical device of claim 5, wherein the neurological stimulation device is programmed to selectively provide a plurality of therapeutic treatments to a patient.

7. The medical device of claim 1, wherein the medical device is selected from the group consisting of a cardiac defibrillator, a cardiac pacemaker, a cardiac contractility module, a cardiac contractility modulator, a cardioverter, a drug administration device, a cochlear implant, a hearing aid, a sensor, a telemetry device, and a diagnostic recorder.

8. The medical device of claim 7, wherein the medical device is an implantable cardiac defibrillator for providing a therapeutic high voltage treatment to a patient.

9. The medical device of claim 8, further comprising at least one lead extending from the cardiac defibrillator and configured to electrically stimulate a portion of a patient's heart.

10. The medical device of claim 1, wherein the negative current collector comprises aluminum.

11. The medical device of claim 10, wherein the positive current collector comprises aluminum.

12. The medical device of claim 10, wherein the negative current collector comprises an aluminum alloy.

13. The medical device of claim 1, further comprising a battery case in contact with the negative electrode, the battery case comprising aluminum.

14. The medical device of claim 1, wherein the active material of the negative electrode comprises a conductive material for providing increased conductivity for the negative electrode.

15. The medical device of claim 14, wherein the conductive material comprises carbon.

16. The medical device of claim 1, wherein the lithium titanate material comprises $Li_4Ti_5O_{12}$.

17. The medical device of claim 1, wherein the polymeric separator provided intermediate the positive electrode and the negative electrode comprises a copolymer of polypropylene and polyethylene.

18. The medical device of claim 1, wherein the battery has a capacity between approximately 10 mAh and 1000 mAh.

19. The medical device of claim 1, wherein the battery has a capacity of approximately 300 mAh.

20. A device for providing at least one of a therapeutic treatment and a diagnostic function to a patient comprising:
a rechargeable battery for providing power to the device, the battery comprising:
a positive electrode comprising a current collector and an active material comprising a material selected from the group consisting of $LiCoO_2$, $LiMn_2O_4$, $LiNi_{1/3}Co_{1/3}Mn_{1/3}O_2$, $LiAl_xCo_yNi_{(1-x-y)}O_2$ where x is between approximately 0.05 and 0.3 and y is between approximately 0.1 and 0.3, $LiTi_xCo_yNi_{(1-x-y)}O_2$ where x is between approximately 0.05 and 0.3 and y is between approximately 0.1 and 0.3, and combinations thereof;
a negative electrode comprising a negative current collector provided as a foil and an active material provided on the negative current collector, the negative current collector comprising aluminum and the active material provided on the negative current collector comprising a lithium titanate material;
a liquid electrolyte; and
a separator comprising a polymeric material provided between the positive electrode and the negative electrode, the separator comprising a polyolefin laminate.

21. The device of claim 20, wherein at least a portion of the device is configured for implantation into a body of a patient.

22. The device of claim 21, wherein the device comprises a neurological stimulation device.

23. The device of claim 22, wherein the neurological stimulation device is programmed to selectively provide a plurality of therapeutic treatments to a patient.

24. The device of claim 21, wherein the device is selected from the group consisting of a cardiac defibrillator, a cardiac pacemaker, a cardioverter, a cardiac contractility modulator, a drug administration device, a cochlear implant, a hearing aid, a sensor, a telemetry device, and a diagnostic recorder.

25. The device of claim 24, wherein the device is an implantable cardiac defibrillator for providing a therapeutic high voltage treatment to a patient.

26. The device of claim 21, wherein the current collector of the positive electrode comprises aluminum.

27. The device of claim 21, wherein the negative current collector comprises an aluminum alloy.

28. The device of claim 21, further comprising a battery housing in contact with the negative electrode, the battery housing comprising aluminum.

29. The device of claim 21, wherein the active material of the negative electrode further comprises a conductive material for providing increased conductivity for the negative electrode.

30. The device of claim 29, wherein the conductive material comprises carbon.

31. The device of claim 21, wherein the lithium titanate material comprises $Li_4Ti_5O_{12}$.

32. The device of claim 21, wherein the positive electrode and the negative electrode have a zero voltage crossing potential above the decomposition potential of the $LiCoO_2$ active material.

33. The device of claim 32, wherein the zero voltage crossing potential is approximately 3.8 volts.

34. The device of claim 21, wherein the separator comprising a polymeric material provided between the positive electrode and the negative electrode includes micropores.

35. The device of claim 21, wherein the battery has a capacity between approximately 10 mAh and 1000 mAh.

36. The device of claim 21, wherein the battery has a capacity of approximately 75 mAh.

37. A system for providing at least one of a therapeutic treatment and a diagnostic function to a patient comprising:
a lithium-ion battery configured to provide power to the system and being capable of being charged and discharged, the lithium-ion battery comprising:
a positive electrode comprising an aluminum current collector and an active material provided in contact with the aluminum current collector and selected from the group consisting of $LiCoO_2$, $LiMn_2O_4$, $LiNi_{1/3}Co_{1/3}Mn_{1/3}O_2$, $LiAl_xCo_yNi_{(1-x-y)}O_2$ where x is between approximately 0.05 and 0.3 and y is between approximately 0.1 and 0.3, $LiTi_xCO_yNi_{(1-x-y)O2}$ where x is between approximately 0.05 and 0.3 and y is between approximately 0.1 and 0.3, and combinations thereof;

a negative electrode comprising an aluminum foil current collector and an active material, the active material provided on the current collector of the negative electrode comprising $Li_4Ti_5O_{12}$;

a liquid electrolyte; and a polymeric separator provided intermediate the positive electrode and the negative electrode, the polymeric separator comprising a polyolefin laminate that includes pores;

wherein the positive electrode and the negative electrode have a zero voltage crossing potential above a decomposition potential of the $LiCoO_2$ active material.

38. The system of claim 37, wherein at least a portion of the medical device is implanted into a body of a patient.

39. The system of claim 38, wherein the lithium-ion battery may be charged without removing the medical device from the body of the patient.

40. The system of claim 37, wherein the system comprises a neurological stimulation device.

41. The system of claim 37, wherein the system includes a device selected from the group consisting of a cardiac defibrillator, a cardiac pacemaker, a cardioverter, a cardiac contractility modulator, a drug administration device, a cochlear implant, a hearing aid, a sensor, a telemetry device, and a diagnostic recorder.

42. The system of claim 41, wherein the device is an implantable cardiac defibrillator for providing a therapeutic high voltage treatment to a patient.

43. The system of claim 37, wherein the positive electrode and the negative electrode have zero voltage below a corrosion potential of the aluminum current collector of the negative electrode.

44. The system of claim 37, wherein the polymeric separator provided intermediate the positive electrode and the negative electrode comprises a copolymer of polypropylene and polyethylene.

45. The system of claim 37, further comprising a battery casing in contact with the negative electrode, the battery housing comprising aluminum.

46. The system of claim 37, wherein the battery has a capacity between approximately 10 mAh and 1000 mAh.

* * * * *

UNITED STATES PATENT AND TRADEMARK OFFICE
CERTIFICATE OF CORRECTION

PATENT NO. : 7,682,745 B2  Page 1 of 1
APPLICATION NO. : 10/978712
DATED : March 23, 2010
INVENTOR(S) : William G. Howard, Craig L. Schmidt and Erik R. Scott It is certified that error appears in the above-identified patent and that said Letters Patent is hereby corrected as shown below:

Column 19:
lines 1-2, replace "$LiTi_xCO_yNi_{(1-x-y)O2}$" with --$LiTi_xCO_yNi_{(1-x-y)}O_2$--.

Signed and Sealed this

Fourth Day of May, 2010

David J. Kappos
*Director of the United States Patent and Trademark Office*